United States Patent
Luke et al.

(10) Patent No.: US 11,795,168 B2
(45) Date of Patent: Oct. 24, 2023

(54) INHIBITING CYCLIC AMP-RESPONSIVE ELEMENT-BINDING PROTEIN (CREB) BINDING PROTEIN (CBP)

(71) Applicant: FORMA Therapeutics, Inc., Watertown, MA (US)

(72) Inventors: George Luke, Clinton, CT (US); Suresh Babu, Ypsilanti, MI (US)

(73) Assignee: Forma Therapeutics, Inc., Watertown, MA (US)

( * ) Notice: Subject to any disclaimer, the term of this patent is extended or adjusted under 35 U.S.C. 154(b) by 0 days.

(21) Appl. No.: 17/482,717

(22) Filed: Sep. 23, 2021

(65) Prior Publication Data

US 2022/0089594 A1    Mar. 24, 2022

Related U.S. Application Data

(60) Provisional application No. 63/082,168, filed on Sep. 23, 2020.

(51) Int. Cl.
*C07D 471/04* (2006.01)
*A61K 9/48* (2006.01)
*A61K 9/16* (2006.01)

(52) U.S. Cl.
CPC .......... *C07D 471/04* (2013.01); *A61K 9/1611* (2013.01); *A61K 9/1617* (2013.01); *A61K 9/1623* (2013.01); *A61K 9/1635* (2013.01); *A61K 9/1652* (2013.01); *A61K 9/485* (2013.01); *A61K 9/4858* (2013.01); *A61K 9/4866* (2013.01)

(58) Field of Classification Search
CPC ..... C07D 471/04; A61K 9/4858; A61K 9/485
USPC ........................................................ 514/293
See application file for complete search history.

(56) References Cited

U.S. PATENT DOCUMENTS

| | | | |
|---|---|---|---|
| 6,011,029 A | 1/2000 | Ding et al. | |
| 7,101,869 B2 | 9/2006 | Blumenkopf et al. | |
| 7,709,489 B2 | 5/2010 | Aranyi et al. | |
| 9,211,333 B2 | 12/2015 | Zhang et al. | |
| 9,763,922 B2 | 9/2017 | Adler et al. | |
| 9,975,896 B2 | 5/2018 | Marineau et al. | |
| 10,336,722 B2 | 7/2019 | Bair et al. | |
| 10,562,916 B2 | 2/2020 | Campbell et al. | |
| 10,870,648 B2 * | 12/2020 | Schiller | A61P 35/00 |
| 2004/0214825 A1 | 10/2004 | McCall et al. | |
| 2006/0106020 A1 | 5/2006 | Rodgers et al. | |
| 2006/0167047 A1 | 7/2006 | Timmers et al. | |
| 2007/0179165 A1 | 8/2007 | Gyorkos et al. | |
| 2007/0203236 A1 | 8/2007 | Smith et al. | |
| 2007/0254961 A1 | 11/2007 | Tapas et al. | |
| 2009/0326020 A1 | 12/2009 | Yan et al. | |
| 2010/0166781 A1 | 7/2010 | Setiadi et al. | |
| 2010/0179325 A1 | 7/2010 | Suzuki et al. | |
| 2010/0216853 A1 | 8/2010 | Marmorstein et al. | |
| 2010/0267672 A1 | 10/2010 | Jung et al. | |
| 2011/0257196 A1 | 10/2011 | Yan et al. | |
| 2012/0108581 A1 | 5/2012 | Ashikawa et al. | |
| 2012/0258953 A1 | 10/2012 | Aay et al. | |
| 2013/0158003 A1 | 6/2013 | Campbell et al. | |
| 2013/0324580 A1 | 12/2013 | Zhang et al. | |
| 2016/0158207 A1 | 9/2016 | Adler et al. | |
| 2016/0257692 A1 | 9/2016 | Bair et al. | |
| 2020/0216445 A1 | 7/2020 | Schiller et al. | |

FOREIGN PATENT DOCUMENTS

| | | |
|---|---|---|
| EP | 2 412 710 A1 | 1/2012 |
| JP | 2013-526615 | 6/2013 |
| JP | 2016-540831 | 12/2016 |
| JP | 2017-537100 | 12/2017 |
| WO | WO 1995/020589 A1 | 8/1995 |
| WO | WO 2002/040614 A1 | 5/2002 |
| WO | WO 2003/033517 A1 | 4/2003 |
| WO | WO 2003/045929 A1 | 6/2003 |
| WO | WO 2004/043392 A2 | 5/2004 |
| WO | WO 2005/066162 A1 | 7/2005 |
| WO | WO 2007/120339 A1 | 10/2007 |
| WO | WO 2007/133653 A2 | 11/2007 |
| WO | WO 2008/009348 A1 | 1/2008 |
| WO | WO 2009/000413 A1 | 12/2008 |
| WO | WO 2009/064251 A1 | 5/2009 |
| WO | WO 2009/152072 A1 | 12/2009 |
| WO | WO 2010/110380 A1 | 9/2010 |
| WO | WO 2010/118208 A1 | 10/2010 |
| WO | WO 2010/138490 A1 | 12/2010 |

(Continued)

OTHER PUBLICATIONS

Extended European Search Report from corresponding application EP 19 18 3741 (dated Aug. 1, 2019).
International Search Report from related application PCT/US2018/051235 (dated Feb. 25, 2019).
International Search Report from related application PCT/US2018/051214 (dated Dec. 4, 2018).
International Search Report from related application PCT/US2017/034320 (dated Nov. 15, 2017).
International Search Report from related application PCT/US2014/066198 (dated May 18, 2015).

(Continued)

*Primary Examiner* — Niloofar Rahmani
(74) *Attorney, Agent, or Firm* — Wiggin and Dana LLP

(57) ABSTRACT

The present disclosure is directed to solid and salt forms of inhibitors of the CBP/p300 family of bromodomains made up of salts and crystalline forms of Formula (I). The compounds can be useful in the treatment of disease or disorders associated with the inhibition of the CBP/p300 family of bromodomains. For instance, the disclosure is concerned with compounds and compositions for inhibition of the CBP/p300 family of bromodomains, methods of treating diseases or disorders associated with the inhibition of CBP/p300 family of bromodomains (e.g., certain forms of cancer), and methods of synthesis of these compounds.

19 Claims, 6 Drawing Sheets

(56) References Cited

FOREIGN PATENT DOCUMENTS

| WO | WO 2011/085039 A2 | 7/2011 |
|---|---|---|
| WO | WO 2011/109059 A1 | 9/2011 |
| WO | WO 2011/150156 A2 | 12/2011 |
| WO | WO 2012/019093 A1 | 2/2012 |
| WO | WO 2012/080729 A2 | 6/2012 |
| WO | WO 2012/082837 A1 | 6/2012 |
| WO | WO 2012/116135 A1 | 8/2012 |
| WO | WO 2013/004995 A1 | 1/2013 |
| WO | WO 2013/006485 A1 | 1/2013 |
| WO | WO 2013/148114 A1 | 10/2013 |
| WO | WO 2014/045305 A1 | 3/2014 |
| WO | WO 2014/133414 A2 | 9/2014 |
| WO | WO 2014/182929 A1 | 11/2014 |
| WO | WO 2015/002754 A2 | 1/2015 |
| WO | WO 2015/004533 A2 | 1/2015 |
| WO | WO 2015/013635 A2 | 1/2015 |
| WO | WO 2015/022322 A1 | 2/2015 |
| WO | WO 2015/073763 A1 | 5/2015 |
| WO | WO 2015/074064 A2 | 5/2015 |
| WO | WO 2015/074081 A1 | 5/2015 |
| WO | WO 2016/044694 A1 | 3/2016 |
| WO | WO 2016/086200 A1 | 6/2016 |
| WO | WO 2016/110821 A1 | 7/2016 |
| WO | WO 2016/128908 A1 | 8/2016 |
| WO | WO 2016/170323 A1 | 10/2016 |
| WO | WO 2016/170324 A1 | 10/2016 |
| WO | WO 2017/197056 A1 | 11/2017 |
| WO | WO 2017/197240 A1 | 11/2017 |
| WO | WO 2017/205536 A2 | 11/2017 |
| WO | WO 2018/073586 A1 | 4/2018 |
| WO | WO 2018/073587 A1 | 4/2018 |
| WO | 2019055869 * | 3/2019 |
| WO | 2019055877 * | 3/2019 |
| WO | WO 2019/055869 A1 | 3/2019 |
| WO | WO 2019/055877 A1 | 3/2019 |
| WO | 2020006483 * | 1/2020 |
| WO | 2020190780 * | 9/2020 |

OTHER PUBLICATIONS

International Search Report from related application PCT/US2019/039936 (dated Sep. 23, 2019).
International Search Report from related application PCT/US2020/022783 (dated Jun. 10, 2020).
International Search Report from related application PCT/US2020/022818 (dated Jun. 15, 2020).
International Search Report from related application PCT/US2020/022823 (dated Jun. 15, 2020).
PubChem CID: 138472436, create date, Aug. 20, 2019, p. 2 formula.
PubChem CID 136574372, deposited Jan. 24, 2019, pp. 1-8, p. 2.
"AR: Anderson Receptor", Depmap Portal, https://depmap.org/portal/gene/AR?tab=characterization (release 19Q2).
"Gene Set: Hallmark_Androgen Response", Gene Set Enrichment Analysis, http://software.broadinstitute.org/gsea/msigdb/cards/HALLMARK_ANDROGEN_RESPONSE.html.
Bowers, et al. Virtual Ligand Screening of the p300/CBP Histone Acetyltransferase: Indentification of a Selective Small Molecule Inhibitor, Chemistry & Biology 17, pp. 471-482, May 28, 2010.
Chekler, Eugene L. et al. "Transcriptional Profiling of a Selective CREB Binding Protein Bromodomain Inhibitor Highlights Therapeutic Opportunities", Chemistry and Biology, 2015, 22(12), 1588-1596.
Crawford et al. "Discovery of a Potent and Selective Vivo Probe (GNE-272) for the Bromodomains to CBP/EP300", J. Med. Chem., 2016, 56 pgs.
Duncan, A. Hay et al. "Discovery and Optimization of Small Molecule Ligands for the CBP/p300 Bromodomains", J. Am. Chem. Soc., 2014, 136(26), 9308-9319.
Fan et al. "p300 Modulates the BRCA1 Inhibition of Estrogen Receptor Activity", Cancer Research, 2002, 62, 141-151.
Garcia-Carpizo et al. "CREBBP/EP300 bromodomain inhibition affects the proliferation of AR positive breast cancer cell lines", Molecular Cancer Research, 2019.
Goff, Corinne Le et al. "Synthesis of some novel fused tetracyclic quinolonecarboxylic acids via 7-methyl-6,7,8,9-tetrahydro-3H-imidazo[4,5-f]quinoline and 6-methyl-5,6,7,8-tetrahydro-1H-imidazo[4,5-g]quinoline", Journal of Heterocyclic Chemistry, 1994, 31(1), 153-160.
Hammitzach, "CBP30, a selective CBP/p300 bromodomain inhibitor, suppresses human Th 17 responses," Proceedings of the National Academy of Science 112.34 (2015): 10768-10773.
Jiang et al., "Small molecule Nas-e targeting cAMP response element binding protein (CREB) and CREB-binding protein interaction inhibits breast cancer bone metastasis" Journal of Cellular and Molecular Medicine, Nov. 20, 2018, vol. 23, pp. 1224-1234.
Jin et al. "Theraoeutic Targeting of the CRP/p300 Bromodomain Blocks the Growth of Castration-Resistant Prostate Cancer", Cancer Research, 2017, 77(20), 5564-5575.
Kumar et al. "Androgen Receptor Immunohistochemistry as a Companion Diagnostic Approach to Predict Clinical Response to Enzalutamide in Triple-Negative Breast Cancer", JCO Precision Oncology, 2017, DOI: 10.1200/PO.17.00075.
Lasko et al. "Discoversy of a selective catalytic p300/CBP inhibitor that targets lineage-specific tumours", Nature, 2017, vol. 000, 17 pgs.
Robinson et al., "Androgen receptor driven transcription in molecular apocrine breast cancer is mediated by FoxA1", The EMBO Journal, 2011, 30, 3019-3027.
Safarpour, Damoun et al. "Androgen receptor (AR) expression in 400 breast carcinomas: is routine AR assessment justified?", Am J Cancer Res, 2014, 4(4), 353-368.
Scher, Howard et al. "Association of AR-V7 on Circulating Tumor Cells as a Treatment-Specific Biomarker with Outcomes and Survival in Castration-Resistant Prostate Cancer," JAMA Oncology, 2016, 2(11), 1441-1449.
Scher et al. "Assessment of the Validity of Nuclear-Localized Androgen Receptor Splice Variant 7 in Circulating Tumor Cells as a Predictive Biomarker for Castration-Resistant Prostate Cancer" JAMA Oncology, 2018, 4(9), 1179-1186.
Snow et al., "Discovery of 2-Phenylamino-imidazo[4-5-h]isoquinolin-9-ones: a New Class of Inhibitors f Lck Kinase", Journal of Medicinal Chemistry, vol. 45, pp. 3394-3405.
Solankee et al. "Synthesis and evaluation of some novel S-triazine based chalcones and their derivatives",Der Pharma Chemica, 2011, 3(6), 317-324.
Traina et al. "Enzalutamide for the Treatment of Androgen Receptor—Expressing Triple-Negative Breast Cancer" Journal of Clinical Oncology, 2018, 36(9), 884-890.
Tucci, Marcello et al. "Enzalutamide-resistant castration-resistant prostate cancer: challenges and solutions", OncoTargets and Therapy, 2018, 11, 7353-7368.
Wong et al. "Anti-tumor activity of targeted and cytotoxic agents in murine subcutaneous tumor models correlates with clinical response", Clinical Cancer Research, 2012.
European Search Report from corresponding application EP 20 77 3477 (dated Nov. 21, 2022).
Moustakim et al.,, "Discovery of a PCAF Bromodomain Chemical Probe", Angewandte Chemie, Dec. 14, 2016, pp. 845-849, vol. 129.

* cited by examiner

FIGURE 1

A- Parameters for XRPD Analysis

| Parameters | Reflection Mode |
|---|---|
| X-Ray wavelength | Cu, kα<br>Kα1 (Å): 1.540598,<br>Kα2 (Å): 1.544426,<br>Kα2/Kα1 intensity ratio: 0.50 |
| X-Ray tube setting | 45 kV, 40 mA |
| Divergence slit | Fixed 1/8° |
| Scan mode | Continuous |
| Scan range (° 2TH) | 3-40 |
| Scan step time [s] | 18.87 |
| Step size (° 2TH) | 0.0131 |
| Test Time | 4 min 15 s |

B- Parameters for TGA and DSC Analysis

| Parameters | TGA | DSC |
|---|---|---|
| Method | Ramp | Ramp |
| Sample pan | Platinum, open | Aluminum, crimped |
| Temperature | RT - desired temperature | 25 °C - desired temperature |
| Heating rate | 10 °C/min | 10 °C/min |
| Purge gas | $N_2$ | $N_2$ |

FIGURE 1 (continued)

C- Parameters for DVS Analysis

| Parameters | Values |
|---|---|
| Temperature | 25 °C |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 0%RH-95%RH-0%RH |
| RH step size | 10% |

D- Parameters for HPLC Analysis

| Parameters | Values |
|---|---|
| Mobile Phase A | 10 mM Ammonium Acetate |
| Mobile Phase B | Acetonitrile |
| Column | Waters XSelect Phenyl-Hexyl, 3.5 µm, 4.6x150 mm |
| Column Temperature | 35 °C |
| LC Gradient | 0 min 10% B<br>5 min 30% B<br>15 min 45% B<br>21 min 80% B<br>22 min 80% B<br>22.1 min 10% B |
| Runtime | 25 min |
| LC Flow Rate | 1 mL/min |
| UV Wavelength | 238 nm |
| Ionization Mode | Electrospray Ionization- Positive Mode |
| Injection Volume | 8 µL |

FIGURE 2

| | XRPD Peaks for the Hydrochloric Acid Addition Salts | | | | | |
|---|---|---|---|---|---|---|
| | TYPE A | | TYPE B | | TYPE C | |
| Peak No. | Position [°2Θ] | Relative Intensity [%] | Position [°2Θ] | Relative Intensity [%] | Position [°2Θ] | Relative Intensity [%] |
| 1 | 7.27 | 11 | 8.00 | 100 | 7.05 | 7 |
| 2 | 8.98 | 100 | 11.68 | 8 | 8.09 | 100 |
| 3 | 10.60 | 85 | 12.36 | 46 | 9.90 | 7 |
| 4 | 11.44 | 29 | 13.59 | 18 | 11.47 | 9 |
| 5 | 12.05 | 30 | 14.68 | 13 | 11.77 | 6 |
| 6 | 14.54 | 20 | 15.23 | 5 | 12.16 | 16 |
| 7 | 14.93 | 29 | 16.02 | 31 | 12.42 | 17 |
| 8 | 15.60 | 7 | 16.29 | 37 | 13.69 | 5 |
| 9 | 17.51 | 53 | 16.45 | 21 | 14.85 | 15 |
| 10 | 17.69 | 79 | 16.74 | 9 | 16.15 | 7 |
| 11 | 18.01 | 11 | 17.35 | 7 | 16.40 | 20 |
| 12 | 20.17 | 8 | 18.72 | 7 | 16.69 | 9 |
| 13 | 20.44 | 10 | 18.98 | 5 | 16.90 | 8 |
| 14 | 20.59 | 11 | 19.59 | 58 | 17.70 | 14 |
| 15 | 21.35 | 80 | 20.12 | 9 | 19.05 | 17 |
| 16 | 21.67 | 11 | 20.56 | 12 | 19.58 | 7 |
| 17 | 21.88 | 24 | 21.33 | 10 | 19.84 | 47 |
| 18 | 23.24 | 25 | 21.80 | 24 | 20.16 | 5 |
| 19 | 23.46 | 11 | 22.41 | 6 | 21.99 | 21 |
| 20 | 23.93 | 20 | 23.03 | 36 | 23.28 | 27 |
| 21 | 24.26 | 8 | 24.77 | 19 | 24.98 | 22 |
| 22 | 25.33 | 21 | 25.23 | 8 | 25.51 | 9 |
| 23 | 26.79 | 11 | 28.03 | 6 | 28.39 | 6 |
| 24 | 27.12 | 13 | 28.31 | 6 | 31.44 | 8 |
| 25 | 27.46 | 6 | 31.10 | 8 | | |
| 26 | 28.45 | 12 | 32.68 | 6 | | |
| 27 | 29.38 | 6 | | | | |
| 28 | 30.08 | 22 | | | | |
| 29 | 31.97 | 9 | | | | |
| 30 | 32.67 | 12 | | | | |

FIGURE 3

| | XRPD Peaks for the p-Toluenesulfonic Acid Addition Salts | | | |
|---|---|---|---|---|
| | TYPE A | | TYPE B | |
| Peak No. | Position [°2Θ] | Relative intensity [%] | Position [°2Θ] | Relative intensity [%] |
| 1 | 5.78 | 5 | 7.10 | 100 |
| 2 | 6.59 | 100 | 9.15 | 27 |
| 3 | 13.20 | 6 | 9.70 | 6 |
| 4 | 13.87 | 26 | 13.54 | 9 |
| 5 | 14.46 | 22 | 13.93 | 14 |
| 6 | 15.77 | 5 | 15.08 | 23 |
| 7 | 18.00 | 8 | 15.32 | 14 |
| 8 | 19.01 | 8 | 16.19 | 17 |
| 9 | 19.83 | 10 | 17.25 | 31 |
| 10 | 20.27 | 27 | 18.31 | 15 |
| 11 | 21.74 | 10 | 18.73 | 12 |
| 12 | | | 19.04 | 10 |
| 13 | | | 19.96 | 16 |
| 14 | | | 20.30 | 6 |
| 15 | | | 22.13 | 19 |
| 16 | | | 22.45 | 8 |
| 17 | | | 23.16 | 9 |
| 18 | | | 23.47 | 5 |
| 19 | | | 24.31 | 7 |
| 20 | | | 25.26 | 16 |
| 21 | | | 28.45 | 5 |

FIGURE 4

| XRPD Peaks for the Type A Benzenesulfonic Acid Addition Salt | | | | | |
|---|---|---|---|---|---|
| Peak No. | Position [°2Θ] | Relative intensity [%] | Peak No. | Position [°2Θ] | Relative intensity [%] |
| 1 | 5.84 | 20 | 10 | 17.61 | 7 |
| 2 | 7.48 | 100 | 11 | 18.90 | 25 |
| 3 | 9.45 | 21 | 12 | 19.61 | 21 |
| 4 | 13.76 | 10 | 13 | 20.70 | 17 |
| 5 | 14.94 | 15 | 14 | 22.55 | 6 |
| 6 | 15.22 | 27 | 15 | 22.98 | 8 |
| 7 | 15.87 | 17 | 16 | 23.24 | 20 |
| 8 | 16.05 | 13 | 17 | 25.14 | 13 |
| 9 | 16.84 | 37 | | | |

FIGURE 5

| | XRPD Peaks for the Type A Sulfuric Acid Addition Salt | | | | |
|---|---|---|---|---|---|
| Peak No. | Position [°2Θ] | Relative intensity [%] | Peak No. | Position [°2Θ] | Relative intensity [%] |
| 1 | 8.24 | 85 | 15 | 21.42 | 28 |
| 2 | 9.98 | 42 | 16 | 22.14 | 24 |
| 3 | 10.29 | 12 | 17 | 22.75 | 12 |
| 4 | 11.24 | 14 | 18 | 23.39 | 37 |
| 5 | 11.96 | 27 | 19 | 23.63 | 41 |
| 6 | 13.58 | 39 | 20 | 24.12 | 7 |
| 7 | 14.68 | 36 | 21 | 24.82 | 6 |
| 8 | 15.24 | 28 | 22 | 25.52 | 42 |
| 9 | 16.56 | 100 | 23 | 27.36 | 6 |
| 10 | 16.86 | 31 | 24 | 28.06 | 7 |
| 11 | 17.38 | 11 | 25 | 28.44 | 8 |
| 12 | 18.78 | 49 | 26 | 28.98 | 9 |
| 13 | 19.21 | 11 | 27 | 30.17 | 12 |
| 14 | 20.00 | 52 | | | |

FIGURE 6

| | XRPD Peaks for the Freeform Type A Crystalline Solid | |
|---|---|---|
| Peak No. | Position [°2Θ] | Relative intensity [%] |
| 1 | 11.11 | 26 |
| 2 | 11.40 | 11 |
| 3 | 14.11 | 100 |
| 4 | 14.41 | 24 |
| 5 | 14.91 | 44 |
| 6 | 15.23 | 59 |
| 7 | 18.21 | 6 |
| 8 | 19.00 | 5 |
| 9 | 19.70 | 8 |
| 10 | 19.87 | 16 |
| 11 | 20.48 | 37 |
| 12 | 22.41 | 7 |
| 13 | 23.14 | 34 |
| 14 | 23.20 | 23 |
| 15 | 24.22 | 13 |
| 16 | 25.08 | 14 |
| 17 | 26.24 | 10 |
| 18 | 28.37 | 6 |
| 19 | 28.95 | 7 |

FIGURE 7

Kinetic Solubility Assessments

| Crystal Form (Sample ID) | Media | Solubility (mg/mL) | | | pH | | |
|---|---|---|---|---|---|---|---|
| | | 1 h | 4 h | 24 h | 1 h | 4 h | 24 h |
| Hydrochloric acid addition salt Type A | water | 0.47 | 1.4 | 2.2 | 5.2 | 3.6 | 3.3 |
| | SGF | 3.9 | 4.0 | 3.8 | 2.5 | 1.8 | 1.8 |
| | FaSSIF | 0.65 | 0.61 | 1.4 | 6.3 | 5.9 | 2.1 |
| | FeSSIF | 0.52 | 0.53 | 0.51 | 5.0 | 5.0 | 4.9 |
| p-toluenesulfonic acid addition salt Type B | water | 0.18 | 0.28 | 0.19 | 7.6 | 5.9 | 2.7 |
| | SGF | 0.41 | 0.42 | 0.40 | 2.4 | 2.0 | 1.9 |
| | FaSSIF | 0.67 | 0.60 | 0.17 | 6.1 | 6.3 | 3.2 |
| | FeSSIF | 0.54 | 0.55 | 0.054 | 4.9 | 4.8 | 4.7 |
| Freeform Type A | water | 0.10 | 0.14 | 0.20 | 8.9 | 8.9 | 8.7 |
| | SGF | 2.8 | 2.4 | 2.2 | 1.9 | 2.0 | 1.9 |
| | FaSSIF | 0.087 | 0.088 | 0.090 | 6.7 | 6.7 | 6.7 |
| | FeSSIF | 0.040 | 0.040 | 0.050 | 5.1 | 5.1 | 5.1 |

INHIBITING CYCLIC AMP-RESPONSIVE ELEMENT-BINDING PROTEIN (CREB) BINDING PROTEIN (CBP)

CROSS-REFERENCE TO RELATED APPLICATIONS

This application claims the benefit of U.S. Provisional Application No. 63/082,168, filed Sep. 23, 2020, which is incorporated herein by reference in its entirety.

TECHNICAL FIELD

The present disclosure relates to solid and salt forms of compounds and methods for the inhibition of p300 (also known as EP300 and KAT3B) binding protein of adenovirus E1A protein, and/or cyclic AMP-responsive element-binding protein (CREB) binding protein (CBP, also known as KAT3A), a cellular paralog of p300. The compounds are useful for the treatment of certain forms of cancer.

BACKGROUND

CBP/p300 are lysine acetyltransferases that catalyze the attachment of an acetyl group to a lysine side chain of histones and other protein substrates. p300 (also known as EP300 and KAT3B) is a protein with multiple domains that bind to diverse proteins including many DNA-binding transcription factors. The cyclic AMP-responsive element-binding protein (CREB) binding protein (CBP, also known as KAT3A) is a cellular paralog of p300. p300 and CBP share extensive sequence identity and functional similarity and are often referred to as CBP/p300. CBP/p300-catalyzed acetylation of histones and other proteins is pivotal to gene activation. Heightened p300 expression and activities have been observed in advanced human cancers such as prostate and in human primary breast cancer specimens. Chemical inhibition of CBP/p300 that possesses intrinsic acetyltransferase enzymatic activity is more feasible than blocking transcription factors with small molecules, as discovery of chemical inhibitors of transcription factors has proven extremely challenging.

Accordingly, there is a need for novel and potent compounds for inhibiting CBP/p300, useful as therapies for treating certain related forms of cancer.

SUMMARY

In one aspect, a non-amorphous, solid form of a compound of formula (I):

(I)

and salts thereof are disclosed.

In another aspect, solid forms of compounds having the stereochemistry of formula (II):

(II)

and salts thereof are disclosed.

In some embodiments, the salt is an acid addition salt selected from hydrochloric acid, p-toluenesulfonic acid, benzenesulfonic acid, and sulfuric acid.

BRIEF DESCRIPTION OF THE DRAWINGS

The present application contains drawings for a better understanding of the principles of the disclosure:

FIG. 1.A is a table of the parameters used for X-ray powder diffraction analysis of the solid forms disclosed herein.

FIG. 1.B is a table of the parameters used for thermogravimetric and differential scanning calorimetry analysis of the solid forms disclosed herein.

FIG. 1.C is a table of the parameters used for dynamic vapor sorption analysis of the solid forms disclosed herein.

FIG. 1.D is a table of the parameters used for the HPLC analysis of the amorphous free base compound disclosed herein.

FIG. 2 is a table of the X-ray powder diffraction peaks with a greater than 5% relative intensity of the type A, B, and C hydrochloric acid addition salt forms disclosed herein.

FIG. 3 is a table of the X-ray powder diffraction peaks with a greater than 5% relative intensity of the type A and B p-toluenesulfonic acid addition slat forms disclosed herein.

FIG. 4 is a table of the X-ray powder diffraction peaks with a greater than 5% relative intensity of the type A benzenesulfonic acid addition salt form disclosed herein.

FIG. 5 is a table of the X-ray powder diffraction peaks with a greater than 5% relative intensity of the type A sulfuric acid addition salt form disclosed herein.

FIG. 6 is a table of the X-ray powder diffraction peaks with a greater than 5% relative intensity of the crystalline freeform type A solid form disclosed herein.

FIG. 7 is a table of the kinetic solubility assessments of the type A hydrochloric acid addition salt form, type B p-toluenesulfonic acid addition salt form, and crystalline freeform type A solid form disclosed herein.

DETAILED DESCRIPTION

The present disclosure relates to salts and solid forms of compounds and compositions that are capable of modulating the activity of the CBP/p300 family bromodomains. The disclosure features methods of treating, preventing or ameliorating a disease or disorder in which CBP/p300 bromodomains play a role by administering to a patient in need thereof a therapeutically effective amount of a compound of Formula (I), (II), or Group A, or a pharmaceutically acceptable salt thereof. The methods of the present disclosure can be used in the treatment of a variety of CBP/p300 bromodomain dependent diseases and disorders by inhibiting the activity of a CBP/p300 bromodomains. Inhibition of CBP/p300 bromodomains provides a novel approach to the treatment of diseases including, but not limited to, cancer.

Salt and crystalline solid forms of drug compounds can confer several distinct advantages over amorphous or non-solid forms, including: 1) increased solubility, dissolution rates, and bioavailability for poorly soluble compounds, 2) decreased solubility for use in extended release formulations, diminished Ostwald ripening, or to accomplish taste masking for particularly soluble compounds, 3) improved physical properties such as melting temperature, hygroscopicity, and mechanical properties, 4) improved chemical stability and compatibility with pharmaceutical excipients, and 5) improved compound purity, chiral resolution of distinct stereoisomers, and filterability.

In certain embodiments, novel CBP Inhibitor Compounds are provided. Unless otherwise indicated, "CBP Inhibitor Compound" as used herein refers to a compound having a detectable CBP $IC_{50}$ value of 1 micromolar or lower when tested according to the HTRF biochemical Assay Protocol of Example 3.

Unless otherwise indicated herein, all isomeric forms of specified chemical compounds are provided by the present disclosure, including mixtures thereof (e.g., S, R and racemic orientations at each chiral center). If the compound contains a double bond, the substituent may be in the E or Z configuration. If the compound contains a disubstituted cycloalkyl, the cycloalkyl substituent may have a cis- or trans-configuration. All tautomeric forms are also intended to be included.

Compounds of Formula (I), (II), and Group A, unless otherwise indicated, may exist in their tautomeric form. All such tautomeric forms are contemplated herein as part of the present disclosure.

The compounds of Formula (I), (II), and Group A, unless otherwise indicated, may contain one or more stereocenters, and, therefore, exist in different stereoisomeric forms. It is intended that unless otherwise indicated all stereoisomeric forms of the compounds of Formula (I), (II), and Group A, as well as mixtures thereof, including racemic mixtures, form part of the present disclosure. In addition, the present disclosure embraces all geometric and positional isomers. For example, if a compound of Formula (I), (II), or Group A incorporates a double bond or a fused ring, both the cis- and trans-forms, as well as mixtures, are embraced within the scope of the disclosure. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I), (II), or Group A may be atropisomers (e.g., substituted biaryls) and are considered as part of this disclosure. Enantiomers can also be separated by use of a chiral HPLC column.

The compounds of Formula (I), (II), or Group A may form acid addition salts, which may be pharmaceutically acceptable salts. The disclosure also includes pharmaceutical compositions comprising one or more compounds as described herein, or a pharmaceutically acceptable salt thereof, and a pharmaceutically acceptable carrier. In some embodiments, pharmaceutical compositions reported herein can be provided in a unit dosage form (e.g., capsule, tablet or the like). In some embodiments, pharmaceutical compositions reported herein can be provided in an oral dosage form. In some embodiments, an oral dosage form of a compound of Formula (I), (II), or Group A can be a capsule. In some embodiments, an oral dosage form of a compound of Formula (I), (II), or Group A is a tablet. In some embodiments, an oral dosage form comprises one or more fillers, disintigrants, lubricants, glidants, anti-adherents and/or anti-statics. In some embodiments, an oral dosage form is prepared via dry blending. In some embodiments, an oral dosage form is a tablet and is prepared via dry granulation.

In some embodiments, the pharmaceutical composition includes one or more pharmaceutically acceptable excipients selected from the group consisting of fillers, surfactants, disintegrants, glidants, and lubricants. In some embodiments, the pharmaceutical composition includes one or more fillers including Avicel PH 101 and Mannitol M200. In some embodiments, the pharmaceutical composition includes one or more fillers selected from Avicel PH 101 and Mannitol M200. In some embodiments, the pharmaceutical composition includes one or more surfactants including sodium lauryl sulfate. In some embodiments, the pharmaceutical composition includes one or more disintegrants including Ac-Di-Sol and Kollidon CL. In some embodiments, the pharmaceutical composition includes one or more disintegrants selected from Ac-Di-Sol and Kollidon CL. In some embodiments, the pharmaceutical composition includes one or more glidants including fumed silica. In some embodiments, the pharmaceutical composition includes one or more lubricants including magnesium stearate. In some embodiments, the pharmaceutical composition may be a capsule formulation, as described in Example 5 herein. In other embodiments, the pharmaceutical composition may be a capsule formulation as described in Example 6 herein.

In some embodiments, a pharmaceutical composition includes Compound 1 in a micronized form. In some embodiments, a pharmaceutical composition includes the Type A hydrochloric acid addition salt of Compound 1 in a micronized form. In some embodiments, the micronized form demonstrates a more uniform particle size distribution, where the particles have a reduced average particle size, as compared to an unmicronized form of Compound 1.

In some embodiments, a pharmaceutical composition including Compound 1 includes Compound 1 in a granulated blend form. In some embodiments, a pharmaceutical composition including Compound 1 is in a granulated blend form, where Compound 1 is provided as the Type A hydrochloric acid addition salt of Compound 1. In some embodiments, the pharmaceutical composition in a granulated blend form demonstrates an improved dissolution profile, compared to a non-granulated blend. In some embodiments, an improved dissolution profile includes the more rapid dissolution of the pharmaceutical composition in a simulated gastric fluid.

A CBP Inhibitor compound of the present disclosure can be dosed at a therapeutically effective level.

Compounds of the Disclosure

The present disclosure relates to solid forms of compounds, or pharmaceutically acceptable salts or isomers thereof, capable of modulating CBP/p300 family bromodomains which are useful for the treatment of diseases and disorders associated with modulation of CBP/p300 family bromodomains. The disclosure further relates to solid forms of compounds, or pharmaceutically acceptable salts or isomers thereof, which are useful for inhibiting CBP/p300 family bromodomains.

In one aspect, the disclosure relates to a solid form of a compound of Formula (I)

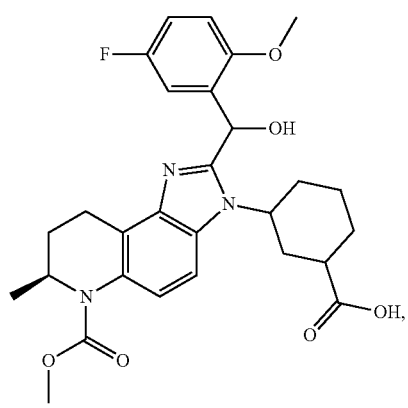

(I)

and enantiomers, hydrates, solvates, isomers, and tautomers thereof and acid addition salts of the foregoing.

In some embodiments, the disclosure relates to solid and salt forms selected from one or more of Group A:

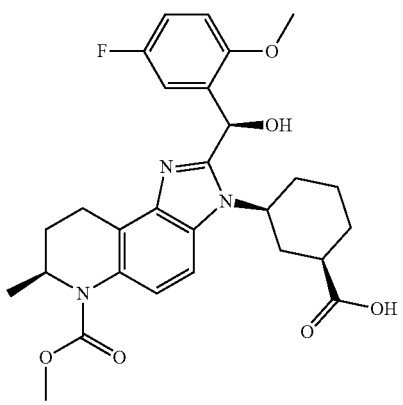

(A1)

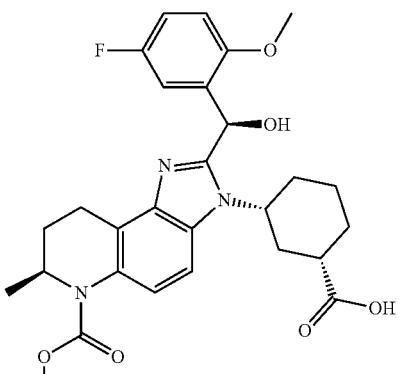

(A2)

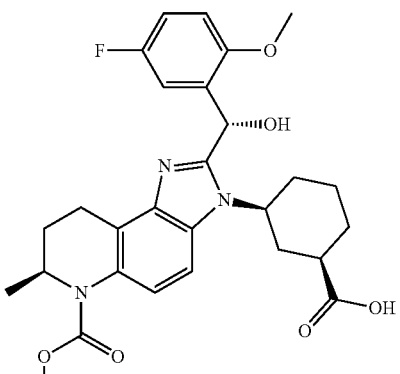

(A3)

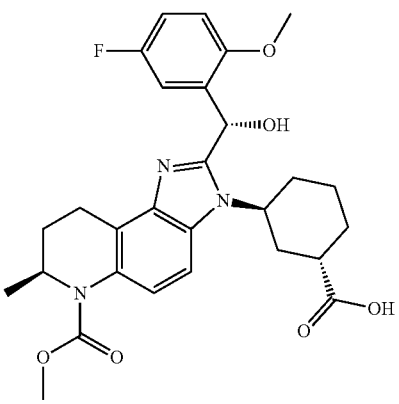

(A4)

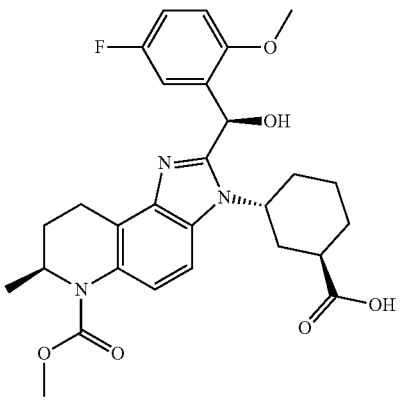

(A5)

(A6)
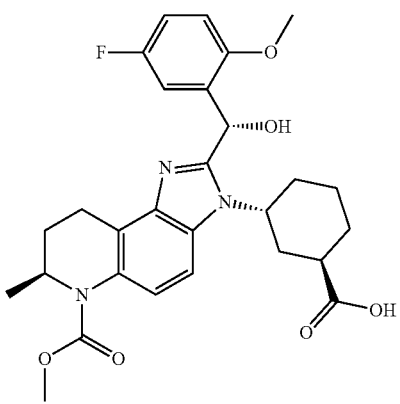

(A7)
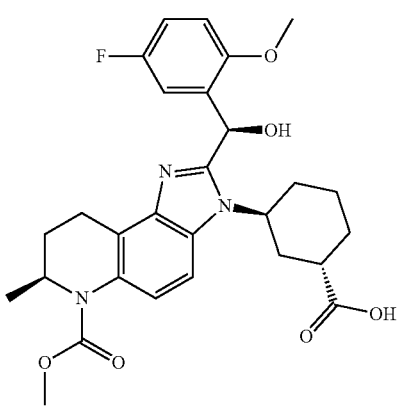

(A8)
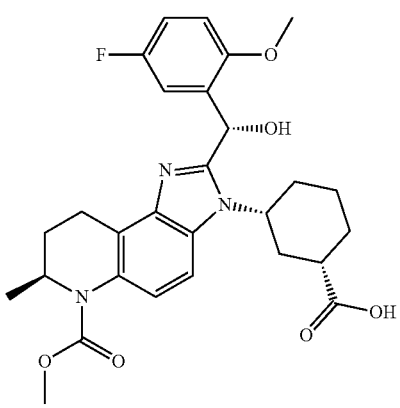

and enantiomers, hydrates, solvates, and tautomers thereof and acid addition salts of the foregoing.

In a preferred form, the present disclosure relates to solid and salt forms of Formula (II):

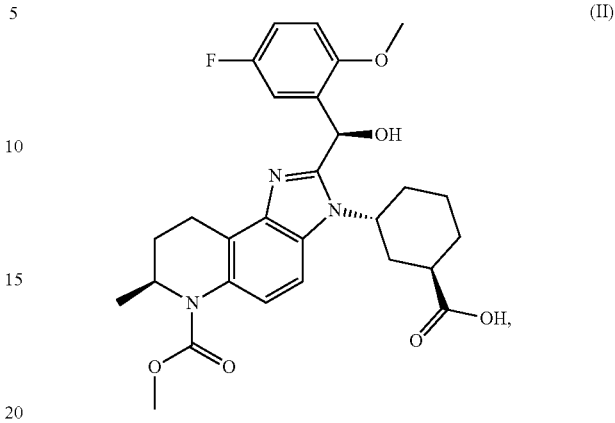

(II)

and enantiomers, hydrates, solvates, and taumers thereof, and acid addition salts of the foregoing.

The acid addition salts of the foregoing may originate from the addition of hydrochloric acid (HCl), p-toluenesulfonic acid, benzenesulfonic acid, and sulfuric acid ($H_2SO_4$). In the absence of an acid addition salt, the compounds are referred to as a free base form. The acid addition salts and free base forms may be crystalline.

The free base form may not be amorphous in some embodiments. The amorphous, free base form is accessed through a synthesis provided in Example 1. This chemical synthesis produces the compound of formula (II) with substantial purity. Only trace amounts of the stereoisomeric contaminants of Group A are present in the end synthetic product, with the exception of compound A6, which is present in quantifiable amounts. The amorphous, free base form is produced with purities in excess of 99%, as determined by HPLC analysis as outlined in the examples below.

With respect to solid forms of a hydrochloric acid addition salt, applicant discovered three crystalline forms (hereafter referred to as types A, B, and C), two crystalline forms of a p-toluenesulfonic acid addition salt (hereafter referred to as types A and B), one crystalline form of a benzenesulfonic acid addition salt (hereafter referred to as type A), one form of a sulfuric acid addition salt (hereafter referred to as type A), and a free base crystalline form (hereafter referred to as freeform type A) of the compounds of Formula (I).

HCl Addition Salt Forms

Type A

Crystalline type A of the hydrochloric acid addition salt is characterized by an X-ray powder diffraction pattern (XRPD) having at least three approximate peak positions (degrees 2θ±0.2), when measured using Cu $K_\alpha$ radiation, selected from the group consisting of: 7.27, 8.98, 10.60, 15.60, and 23.93, when the XRPD is collected from about 3 to about 40 degrees 2θ. FIG. 2 contains a list of peaks from the X-ray powder diffraction pattern of the type A hydrochloric acid addition salt having a relative intensity greater than or equal to 5%.

In some embodiments, crystalline type A of the hydrochloric acid addition salt is characterized by an X-ray power diffraction pattern (XRPD) having at least three approximate peak positions (degrees 2θ±0.2), when measured using Cu $K_\alpha$ radiation, selected from the group consisting of: 7.27, 8.98, 10.60, 11.44, 12.05, 14.54, 14.93, 15.60, 17.51, 17.69, 18.01, 20.17, 20.44, 20.59, 21.35, 21.67, 21.88, 23.24, 23.46, 23.93, 24.26, 25.33, 26.79, 27.12, 27.46, 28.45, 29.38, 30.08, 31.97, and 32.67.

In some embodiments, crystalline type A of the hydrochloric acid addition salt is characterized by an X-ray power diffraction pattern (XRPD) having at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, at least twenty-seven, at least twenty-eight, at least twenty-nine, or thirty approximate peak positions (degrees 2θ±0.2), when measured using Cu $K_\alpha$ radiation, selected from the group consisting of: 7.27, 8.98, 10.60, 11.44, 12.05, 14.54, 14.93, 15.60, 17.51, 17.69, 18.01, 20.17, 20.44, 20.59, 21.35, 21.67, 21.88, 23.24, 23.46, 23.93, 24.26, 25.33, 26.79, 27.12, 27.46, 28.45, 29.38, 30.08, 31.97, and 32.67.

In some embodiments, crystalline type A of the hydrochloric acid addition salt is characterized by an X-ray power diffraction pattern (XRPD) having at least three approximate peak positions (degrees 2θ±0.2), when measured using Cu $K_\alpha$ radiation, selected from the group consisting of: 7.27, 8.98, 10.60, 15.60, 18.01, 23.93, 26.79, 27.12, 30.08, and 31.97.

In some embodiments, crystalline type A of the hydrochloric acid addition salt is characterized by an X-ray power diffraction pattern (XRPD) having at least four, at least five, at least six, at least seven, at least eight, at least nine, or ten approximate peak positions (degrees 2θ±0.2), when measured using Cu $K_\alpha$ radiation, selected from the group consisting of: 7.27, 8.98, 10.60, 15.60, 18.01, 23.93, 26.79, 27.12, 30.08, and 31.97.

It is also characterized by an endothermic peak having an onset temperature at about 230° C. as measured by differential scanning calorimetry (DSC). The HCl type A salt is also characterized by a weight loss of approximately 1.1% at temperatures up to 170° C., as measured by thermogravimetric analysis. The HCl type A salt is also characterized as hygroscopic, evidenced by the water uptake of 6.3% at relative humidity of up to 80%, as measured by dynamic vapor sorption isotherm plots. In another embodiment, the type A hydrochloric acid addition salt is characterized by the kinetic solubility data shown below in Example 2. The type A hydrochloric acid addition salt can be stable for at least two weeks at temperatures up to 40° C. and relative humidity of up to 75%.

Crystalline type A of the hydrochloric acid addition salt is an anhydrate (anhydrous).

The crystalline type A of the hydrochloric acid addition salt can be prepared by dissolving the free base form in an organic solvent, adding hydrochloric acid, heating the resulting solution followed by cooling, as provided in Example 1.b.

Type B

Crystalline type B of the hydrochloric acid addition salt is characterized by an X-ray powder diffraction pattern (XRPD) having at least three approximate peak positions (degrees 2θ±0.2), when measured using Cu $K_\alpha$ radiation, selected from the group consisting of: 10.23, 18.72, 23.03, 24.77, and 28.03, when the XRPD is collected from about 3 to about 40 degrees 2θ. FIG. 2 contains a list of peaks from the X-ray powder diffraction pattern of the type B hydrochloric acid addition salt having a relative intensity greater than or equal to 5%.

In some embodiments, crystalline type B of the hydrochloric acid addition salt is characterized by an X-ray power diffraction pattern (XRPD) having at least three approximate peak positions (degrees 2θ±0.2), when measured using Cu $K_\alpha$ radiation, selected from the group consisting of: 8.00, 11.68, 12.36, 13.59, 14.68, 15.23, 16.02, 16.29, 16.45, 16.74, 17.35, 18.72, 18.98, 19.59, 20.12, 20.56, 21.33, 21.80, 22.41, 23.03, 24.77, 25.23, 28.03, 28.31, 31.10, and 32.68.

In some embodiments, crystalline type B of the hydrochloric acid addition salt is characterized by an X-ray power diffraction pattern (XRPD) having at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, or twenty-six approximate peak positions (degrees 2θ±0.2), when measured using Cu $K_\alpha$ radiation, selected from the group consisting of: 8.00, 11.68, 12.36, 13.59, 14.68, 15.23, 16.02, 16.29, 16.45, 16.74, 17.35, 18.72, 18.98, 19.59, 20.12, 20.56, 21.33, 21.80, 22.41, 23.03, 24.77, 25.23, 28.03, 28.31, 31.10, and 32.68.

In some embodiments, crystalline type B of the hydrochloric acid addition salt is characterized by an X-ray power diffraction pattern (XRPD) having at least three approximate peak positions (degrees 2θ±0.2), when measured using Cu $K_\alpha$ radiation, selected from the group consisting of: 10.23, 13.59, 15.23, 17.35, 18.72, 22.41, 23.03, 24.77, 28.03, and 31.10.

In some embodiments, crystalline type B of the hydrochloric acid addition salt is characterized by an X-ray power diffraction pattern (XRPD) having at least four, at least five, at least six, at least seven, at least eight, at least nine, or ten approximate peak positions (degrees 2θ±0.2), when measured using Cu $K_\alpha$ radiation, selected from the group consisting of: 10.23, 13.59, 15.23, 17.35, 18.72, 22.41, 23.03, 24.77, 28.03, and 31.10.

It is also characterized by endothermic peaks having onset temperatures at about 139° C. and 232° C. and an exothermic peak at about 104° C. as measured by DSC. The HCl type B salt is also characterized by a weight loss of approximately 20% at temperatures up to 200° C., as measured by thermogravimetric analysis.

In some embodiments, crystalline type B of the hydrochloric acid addition salt is a hydrate or solvate.

The crystalline type B of the hydrochloric acid addition salt can be prepared by dissolving the type A hydrochloric acid addition salt in a mixture of organic solvents, and then heating the resulting solution, followed by cooling and slow evaporation at room temperature as provided in Example 1.c.

Type C

Crystalline type C of the hydrochloric acid addition salt is characterized by an X-ray powder diffraction pattern (XRPD) having at least three approximate peak positions (degrees 2θ±0.2), when measured using Cu $K_\alpha$ radiation, selected from the group consisting of: 7.05, 19.84, 21.09, 24.98, and 31.44, when the XRPD is collected from about 3 to about 40 degrees 2θ. FIG. 2 contains a list of peaks from the X-ray powder diffraction pattern of the type B hydrochloric acid addition salt having a relative intensity greater than or equal to 5%.

In some embodiments, crystalline type C of the hydrochloric acid addition salt is characterized by an X-ray power diffraction pattern (XRPD) having at least three approximate peak positions (degrees 2θ±0.2), when measured using Cu $K_\alpha$ radiation, selected from the group consisting of: 7.05, 8.09, 9.90, 11.47, 11.77, 12.16, 12.42, 13.69, 14.85, 16.15, 16.40, 16.69, 16.90, 17.70, 19.05, 19.58, 19.84, 20.16, 21.99, 23.28, 24.98, 25.51, 28.39, and 31.44.

In some embodiments, crystalline type C of the hydrochloric acid addition salt is characterized by an X-ray power diffraction pattern (XRPD) having at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, or twenty-four approximate peak positions (degrees 2θ±0.2), when measured using Cu K$_\alpha$ radiation, selected from the group consisting of: 7.05, 8.09, 9.90, 11.47, 11.77, 12.16, 12.42, 13.69, 14.85, 16.15, 16.40, 16.69, 16.90, 17.70, 19.05, 19.58, 19.84, 20.16, 21.99, 23.28, 24.98, 25.51, 28.39, and 31.44.

In some embodiments, crystalline type C of the hydrochloric acid addition salt is characterized by an X-ray power diffraction pattern (XRPD) having at least three approximate peak positions (degrees 2θ±0.2), when measured using Cu K$_\alpha$ radiation, selected from the group consisting of: 7.05, 9.90, 14.85, 16.90, 19.05, 19.84, 21.09, 24.98, 25.51, and 31.44.

In some embodiments, crystalline type C of the hydrochloric acid addition salt is characterized by an X-ray power diffraction pattern (XRPD) having at least four, at least five, at least six, at least seven, at least eight, at least nine, or ten approximate peak positions (degrees 2θ±0.2), when measured using Cu K$_\alpha$ radiation, selected from the group consisting of: 7.05, 9.90, 14.85, 16.90, 19.05, 19.84, 21.09, 24.98, 25.51, and 31.44.

It is also characterized by endothermic peaks having onset temperatures at about 83° C., 143° C., and 179° C. and an exothermic peak at about 230° C. as measured by DSC. The HCl type C salt is also characterized by a weight loss of approximately 9.4% at temperatures up to 180° C., as measured by thermogravimetric analysis.

In some embodiments, crystalline type C of the hydrochloric acid addition salt is a hydrate or solvate.

The crystalline type C of the hydrochloric acid addition salt can be prepared by dissolving the type A hydrochloric acid addition salt in a mixture of organic solvents, and then heating the resulting solution, followed by cooling and slow evaporation at room temperature as provided in Example 1.d.

p-Toluenesulfonic Acid Addition Salt

Type A

Crystalline type A of the p-toluenesulfonic acid addition salt is characterized by an X-ray powder diffraction pattern (XRPD) having at least three approximate peak positions (degrees 2θ±0.2), when measured using Cu K$_\alpha$ radiation, selected from the group consisting of: 6.59, 13.20, 14.46, 18.00, and 21.74, when the XRPD is collected from about 3 to about 40 degrees 2θ. FIG. 3 contains a list of peaks from the X-ray powder diffraction pattern of type A p-toluenesulfonic acid addition salt having a relative intensity greater than or equal to 5%.

In some embodiments, crystalline type A of the p-toluenesulfonic acid addition salt is characterized by an X-ray powder diffraction pattern (XRPD) having at least three approximate peak positions (degrees 2θ±0.2), when measured using Cu K$_\alpha$ radiation, selected from the group consisting of: 5.78, 6.59, 13.20, 13.87, 14.46, 15.77, 18.00, 19.01, 19.83, 20.27, and 21.74.

In some embodiments, crystalline type A of the p-toluenesulfonic acid addition salt is characterized by an X-ray powder diffraction pattern (XRPD) having at least four, at least five, at least six, at least seven, at least eight, at least nine, at least ten, or eleven approximate peak positions (degrees 2θ±0.2), when measured using Cu K$_\alpha$ radiation, selected from the group consisting of: 5.78, 6.59, 13.20, 13.87, 14.46, 15.77, 18.00, 19.01, 19.83, 20.27, and 21.74.

It is also characterized by endothermic peaks having onset temperatures at about 74° C. and 200° C. as measured by DSC. The type A p-toluenesulfonic acid addition salt is also characterized by a weight loss of approximately 1.0% at temperatures up to 180° C., as measured by thermogravimetric analysis.

The crystalline type A p-toluenesulfonic acid addition salt can be prepared by dissolving the free base form in an organic solvent, adding p-toluenesulfonic acid, and heating the resulting solution followed by cooling, as provided in Example 1.e.

Type B

Crystalline type B of the p-toluenesulfonic acid addition salt is characterized by an X-ray powder diffraction pattern (XRPD) having at least three approximate peak positions (degrees 2θ±0.2), when measured using Cu K$_\alpha$ radiation, selected from the group consisting of: 7.10, 9.15, 15.08, 16.19, 17.25, 18.31, and 21.13, when the XRPD is collected from about 3 to about 40 degrees 2θ. FIG. 3 contains a list of peaks from the X-ray powder diffraction pattern of type B p-toluenesulfonic acid addition salt having a relative intensity greater than or equal to 5%.

In some embodiments, crystalline type B of the p-toluenesulfonic acid addition salt is characterized by an X-ray powder diffraction pattern (XRPD) having at least three approximate peak positions (degrees 2θ±0.2), when measured using Cu K$_\alpha$ radiation, selected from the group consisting of: 7.10, 9.15, 9.70, 13.54, 13.93, 15.08, 15.32, 16.19, 17.25, 18.31, 18.73, 19.04, 19.96, 20.30, 22.13, 22.45, 23.16, 23.47, 24.31, 25.26, and 28.45.

In some embodiments, crystalline type C of the hydrochloric acid addition salt is characterized by an X-ray power diffraction pattern (XRPD) having at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, or twenty-one approximate peak positions (degrees 2θ±0.2), when measured using Cu K$_\alpha$ radiation, selected from the group consisting of: 7.10, 9.15, 9.70, 13.54, 13.93, 15.08, 15.32, 16.19, 17.25, 18.31, 18.73, 19.04, 19.96, 20.30, 22.13, 22.45, 23.16, 23.47, 24.31, 25.26, and 28.45.

In some embodiments, crystalline type B of the p-toluenesulfonic acid addition salt is characterized by an X-ray powder diffraction pattern (XRPD) having at least three approximate peak positions (degrees 2θ±0.2), when measured using Cu K$_\alpha$ radiation, selected from the group consisting of: 7.10, 9.15, 15.08, 16.19, 17.25, 18.31, 19.96, 21.13, 22.13, and 25.26.

In some embodiments, crystalline type C of the hydrochloric acid addition salt is characterized by an X-ray power diffraction pattern (XRPD) having at least four, at least five, at least six, at least seven, at least eight, at least nine, or ten approximate peak positions (degrees 2θ±0.2), when measured using Cu K$_\alpha$ radiation, selected from the group consisting of: 7.10, 9.15, 15.08, 16.19, 17.25, 18.31, 19.96, 21.13, 22.13, and 25.26.

It is also characterized by endothermic peak having an onset temperature at about 225° C. as measured by DSC. The type B p-toluenesulfonic acid addition salt is also characterized by a weight loss of approximately 1.3% at temperatures up to 180° C., as measured by thermogravimetric analysis. The type B p-toluenesulfonic acid addition salt is also characterized as hygroscopic, evidenced by the water uptake of 2.1% at relative humidity of up to 80%, as measured by dynamic vapor sorption isotherm plots. The type B p-toluenesulfonic acid addition salt is characterized by the kinetic solubility data shown below in Example 2. The type B p-toluenesulfonic acid addition salt is stable for at least two weeks at temperatures up to 40° C. and relative humidity of up to 75%.

The crystalline type B p-toluenesulfonic acid addition salt can be prepared by dissolving the free base form in an organic solvent, adding p-toluenesulfonic acid, heating the resulting solution followed by cooling, as provided in Example 1.f.

Crystalline type B of the p-toluenesulfonic acid addition salt is an anhydrate (anhydrous).

Benzene Sulfonic Acid Addition Salt Type A

Crystalline type A of the benzenesulfonic acid addition salt is characterized by an X-ray powder diffraction pattern (XRPD) having at least three approximate peak positions (degrees 2θ±0.2), when measured using Cu Kα radiation, selected from the group consisting of: 5.84, 7.48, 9.45, 16.84, 18.90, 19.61, 20.70, and 25.14, when the XRPD is collected from about 3 to about 40 degrees 2θ. FIG. 4 contains a list of peaks from the X-ray powder diffraction pattern of type A benzenesulfonic acid addition salt having a relative intensity greater than or equal to 5%.

In some embodiments, crystalline type A of the benzenesulfonic acid addition salt is characterized by an X-ray powder diffraction pattern (XRPD) having at least three approximate peak positions (degrees 2θ±0.2), when measured using Cu Kα radiation, selected from the group consisting of: 5.84, 7.48, 9.45, 13.76, 14.94, 15.22, 15.87, 16.05, 16.84, 17.61, 18.90, 19.61, 20.70, 22.55, 22.98, 23.24, and 25.14.

In some embodiments, crystalline type A of the benzenesulfonic acid addition salt is characterized by an X-ray powder diffraction pattern (XRPD) having at least four, at least five, at least six, at least seven, at least eight, at least nine, at least ten, at least eleven, at least twelve, at least thirteen, at least fourteen, at least fifteen, at least sixteen, or seventeen approximate peak positions (degrees 2θ±0.2), when measured using Cu Kα radiation, selected from the group consisting of: 5.84, 7.48, 9.45, 13.76, 14.94, 15.22, 15.87, 16.05, 16.84, 17.61, 18.90, 19.61, 20.70, 22.55, 22.98, 23.24, and 25.14.

In some embodiments, crystalline type A of the benzenesulfonic acid addition salt is characterized by an X-ray powder diffraction pattern (XRPD) having at least three approximate peak positions (degrees 2θ±0.2), when measured using Cu Kα radiation, selected from the group consisting of: 5.84, 7.48, 9.45, 15.22, 16.84, 18.90, 19.61, 20.70, 23.24, and 25.14.

In some embodiments, crystalline type A of the benzenesulfonic acid addition salt is characterized by an X-ray powder diffraction pattern (XRPD) having at least four, at least five, at least six, at least seven, at least eight, at least nine, or ten approximate peak positions (degrees 2θ±0.2), when measured using Cu $K_\alpha$ radiation, selected from the group consisting of: 5.84, 7.48, 9.45, 15.22, 16.84, 18.90, 19.61, 20.70, 23.24, and 25.14.

It is also characterized by an endothermic peak having an onset temperature at about 208° C. as measured by DSC. The type A benzenesulfonic acid addition salt is also characterized by negligible weight loss at temperatures up to 210° C., as measured by thermogravimetric analysis.

The crystalline type A benzenesulfonic acid addition salt can be prepared by dissolving the free base form in an organic solvent, adding benzenesulfonic acid, heating the resulting solution followed by cooling, as provided in Example 1.g.

Sulfuric Acid Addition Salt Type A

Crystalline type A of the sulfuric acid addition salt is characterized by an X-ray powder diffraction pattern (XRPD) having at least three approximate peak positions (degrees 2θ±0.2), when measured using Cu Kα radiation, selected from the group consisting of: 8.24, 9.98, 13.58, 16.87, 18.78, 20.00, and 25.52, when the XRPD is collected from about 3 to about 40 degrees 2θ. FIG. 5 contains a list of peaks from the X-ray powder diffraction pattern of type A sulfuric acid addition salt having a relative intensity greater than or equal to 5%.

In some embodiments, crystalline type A of the sulfuric acid addition salt is characterized by an X-ray powder diffraction pattern (XRPD) having at least three approximate peak positions (degrees 2θ±0.2), when measured using Cu Kα radiation, selected from the group consisting of: 8.24, 9.98, 10.29, 11.24, 11.96, 13.58, 14.68, 15.24, 16.56, 16.86, 17.38, 18.78, 19.21, 20.00, 21.42, 22.14, 22.75, 23.39, 23.63, 24.12, 24.82, 25.52, 27.36, 28.06, 28.44, 28.98, and 30.17.

In some embodiments, crystalline type A of the sulfuric acid addition salt is characterized by an X-ray powder diffraction pattern (XRPD) having at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six, or twenty-seven approximate peak positions (degrees 2θ±0.2), when measured using Cu Kα radiation, selected from the group consisting of: 8.24, 9.98, 10.29, 11.24, 11.96, 13.58, 14.68, 15.24, 16.56, 16.86, 17.38, 18.78, 19.21, 20.00, 21.42, 22.14, 22.75, 23.39, 23.63, 24.12, 24.82, 25.52, 27.36, 28.06, 28.44, 28.98, and 30.17.

In some embodiments, crystalline type A of the sulfuric acid addition salt is characterized by an X-ray powder diffraction pattern (XRPD) having at least three approximate peak positions (degrees 2θ±0.2), when measured using Cu Kα radiation, selected from the group consisting of: 8.24, 9.98, 13.58, 15.24 16.87, 18.78, 20.00, 21.42, 23.63 and 25.52.

In some embodiments, crystalline type A of the sulfuric acid addition salt is characterized by an X-ray powder diffraction pattern (XRPD) having at least four, at least five, at least six, at least seven, at least eight, at least nine, or ten approximate peak positions (degrees 2θ±0.2), when measured using Cu Kα radiation, selected from the group consisting of: 8.24, 9.98, 13.58, 15.24 16.87, 18.78, 20.00, 21.42, 23.63 and 25.52.

It is also characterized by endothermic peaks having onset temperatures at about 140° C. and 188° C. as measured by DSC. The type A sulfuric acid addition salt is also characterized by negligible weight loss at temperatures up to 200° C., as measured by thermogravimetric analysis.

The crystalline type A sulfuric acid addition salt can be prepared by dissolving the free base form in an organic solvent, adding sulfuric acid, heating the resulting solution followed by cooling, as provided in Example 1.h.

Free Base Crystalline Form Type A

Crystalline type A free base form is characterized by an X-ray powder diffraction pattern (XRPD) having at least three approximate peak positions (degrees 2θ±0.2), when measured using Cu Kα radiation, selected from the group consisting of: 11.11, 14.11, 18.21, 20.48, and 26.24, when the XRPD is collected from about 3 to about 40 degrees 2θ. FIG. 6 contains a list of peaks from the X-ray powder diffraction pattern of type A free base form having a relative intensity greater than or equal to 5%.

In some embodiments, crystalline type A free base form is characterized by an X-ray powder diffraction pattern (XRPD) having at least three approximate peak positions (degrees 2θ±0.2), when measured using Cu Kα radiation, selected from the group consisting of: 11.11, 11.40, 14.11, 14.91, 15.23, 18.21, 19.00, 19.70, 19.87, 20.48, 22.41, 23.14, 23.20, 24.22, 25.08, 26.24, 28.37, and 28.95.

In some embodiments, crystalline type A free base form is characterized by an X-ray powder diffraction pattern (XRPD) having at least four, at least five, at least six, at least seven, at least eight, at least nine, at least ten, at least eleven, at least twelve, at least thirteen, at least fourteen, at least fifteen, at least sixteen, at least seventeen, at least eighteen, or nineteen approximate peak positions (degrees 2θ±0.2), when measured using Cu Kα radiation, selected from the group consisting of: 11.11, 11.40, 14.11, 14.91, 15.23, 18.21, 19.00, 19.70, 19.87, 20.48, 22.41, 23.14, 23.20, 24.22, 25.08, 26.24, 28.37, and 28.95.

In some embodiments, crystalline type A free base form is characterized by an X-ray powder diffraction pattern (XRPD) having at least three approximate peak positions (degrees 2θ±0.2), when measured using Cu Kα radiation, selected from the group consisting of: 11.11, 14.11, 14.41, 14.91, 18.21, 19.87, 20.48, 23.14, 24.22, and 26.24.

In some embodiments, crystalline type A free base form is characterized by an X-ray powder diffraction pattern (XRPD) having at least four, at least five, at least six, at least seven, at least eight, at least nine, or ten approximate peak positions (degrees 2θ±0.2), when measured using Cu Kα radiation, selected from the group consisting of: 11.11, 14.11, 14.41, 14.91, 18.21, 19.87, 20.48, 23.14, 24.22, and 26.24.

It is also characterized by an endothermic peak having an onset temperature at about 209° C. as measured by DSC. The type A free base form is also characterized by negligible weight loss at temperatures up to 210° C., as measured by thermogravimetric analysis. The type A free base from is characterized by the kinetic solubility data shown below in Example 2.

The crystalline type A free base form can be prepared by dissolving the free base form in an organic solvent at reflux and subsequently cooling the resulting solution, as provided in Example 1.i.

In some embodiments, the salt and crystalline forms used in the preparation of the pharmaceutical compositions are at least 95% pure, as assessed by HPLC analysis.

Method of Synthesizing the Compounds

The compounds of the present disclosure may be made by a variety of methods, including standard chemistry. Suitable synthetic routes are depicted in the examples given below.

The compounds of the present disclosure, i.e., compounds of Formula (I), (II), or Group A or a pharmaceutically acceptable salt thereof, may be prepared by methods known in the art of organic synthesis as set forth in part by the synthetic schemes depicted in the examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I), (II), or Group A.

Those skilled in the art will recognize stereocenters exist in the compounds of Formula (I), (II), or Group A. Accordingly, the present disclosure includes both possible stereoisomers (unless otherwise indicated and/or specified in the synthesis) and includes not only racemic compounds but the individual enantiomers and/or diastereomers as well. Unless otherwise indicated, when a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Methods of Using the Disclosed Compounds

One aspect of the present disclosure relates to a compound of Formula (I), (II), or Group A for use in medicine. Another aspect of the present disclosure relates to a method of modulating one or more of CBP/p300-family bromodomains, comprising administering to a patient in need thereof a therapeutically effective amount of a compound of Formula (I), (II), or Group A. Another aspect of the present disclosure relates to a method of inhibiting one or more of CBP/p300-family bromodomains, comprising administering to a patient in need thereof a therapeutically effective amount of a compound of Formula (I), (II), or Group A. In another aspect, the present disclosure relates to a method of inhibiting one or more of CBP/p300-family bromodomains, comprising administering to a patient in need thereof a therapeutically effective amount of a pharmaceutical composition comprising a compound of Formula (I), (II), or Group A.

CREB binding protein (CBP) Inhibitor Compounds are useful in the development of pharmaceutical compositions suitable for treatment of certain related forms of cancer. CBP Inhibitor Compounds are useful for treating disease states that are responsive to the inhibition of CBP. CBP and EP300 (p300) are closely related multi-domain proteins that function as transcriptional co-activators. They carry acetyl-lysine binding bromodomains which impart a scaffolding or positioning function on these proteins and have proven to be suitable for the design of small molecule inhibitors of their biological function. These paralogs are highly homologous at the amino acid level and share many overlapping functions. They are histone acetyl transferases (HATs) which catalyze the post-translational modification of histone and non-histone proteins. As bromodomain carrying HATs these proteins function as epigenetic readers and writers. The non-histone protein substrates of CBP/p300 consist of numerous transcription factors including nuclear hormone receptors such as the androgen receptor (AR). CBP/p300 function as co-activators of AR-signaling by acetylation of the AR which activates its transcriptional activity and promotes its protein stability. In addition, they acetylate histone H3 at lysine 27 (Ac-H3K27) to provide a docking site for the bromodomain thus providing a scaffold to bridge the nuclear receptor to the basal transcriptional machinery. Acetylation of histone leads to the generation of a transcriptionally permissive environment on chromatin. The localization of CBP/p300 to AR dependent super-enhancers thus leads to increased localized Ac-H3K27 which further increases transcription at these loci.

EXAMPLES

Materials

Unless otherwise noted, all materials were obtained from commercial suppliers and were used without further purification. Anhydrous solvents were obtained from Sigma-Aldrich (Milwaukee, WI) and used directly. All reactions involving air- or moisture-sensitive reagents were performed under a nitrogen atmosphere and all reactions utilizing microwave irradiation were run on a Biotage Initiator EXP EU instrument.

Unless otherwise noted, mass-triggered HPLC purification and/or purity and low resolution mass spectral data were measured using either: (1) Waters Acquity ultra performance liquid chromatography (UPLC) system (Waters Acquity UPLC with Sample Organizer and Waters Micromass ZQ Mass Spectrometer) with UV detection at 220 nm and a low resonance electrospray positive ion mode (ESI) (Column: Acquity UPLC BEH C18 1.7 µm 2.1×50 mm; gradient: 5-100% Solvent B (95/5/0.09%: Acetonitrile/Water/Formic Acid) in Solvent A (95/5/0.1%: 10 mM Ammonium Formate/Acetonitrile/Formic Acid) for 2.2 min then 100-5% Solvent B in Solvent A for 0.01 min then hold at 5% Solvent B in Solvent A for 0.29 min) or (2) Waters HT2790 Alliance high performance liquid chromatography (HPLC) system (Waters 996 PDA and Waters ZQ Single Quad Mass Spectrometer) with UV detection at 220 nm and 254 nm and a low resonance electrospray ionization (positive/negative) mode (ESI) (Column: XBridge Phenyl or C18, 5 µm 4.6×50 mm; gradient: 5-95% Solvent B (95% methanol/5% water with 0.1% Formic Acid) in Solvent A (95% water/5% methanol with 0.1% Formic Acid) for 2.5 min then hold at 95% Solvent B in Solvent A for 1 min (purity and low resolution MS only).

Instruments

In the examples that follow, X-Ray Powder Diffraction (XRPD) was performed with a Panalytical X'Pert3 Powder XRPD on a Si zero-background holder. The 2θ position was calibrated against a Panalytical Si reference standard disc. The XRPD parameters used are listed in FIG. 1A.

Thermogravimetric Analysis (TGA) data were collected using a TA Q500 and Q550 from TA Instruments. Differential Scanning calorimetry (DSC) was performed using a TA Q2000 from TA Instruments. DSC was calibrated with indium reference standard, and the TGA was calibrated using nickel reference standard. Detailed parameters used are listed in FIG. 1B.

Dynamic Vapor Sorption (DVS) data were collected with a SMS DVS Intrinsic from Surface Measurement Systems. Parameters for DVS test are listed in FIG. 1C.

HPLC Assessment of Drug Compound Purity: Drug compound samples for analysis were prepared at concentrations of 0.2 mg/mL in a 70:30 mixture of water and acetonitrile. The samples were subsequently analyzed on a Waters Alliance e2695 liquid chromatography instrument equipped with a Waters QDa mass spectrometer and Waters 2998 photodiode array detector. Parameters for the chromatography method are disclosed in FIG. 1D.

Definitions used in the following Schemes and elsewhere herein are:

Ac-H3K27 acetylated histone H3 at lysine residue 27
AR androgen receptor
BSA bovine serum albumin
CBP cyclic AMP-responsive element binding protein (also known as KAT3A)
DMSO dimethylsulfoxide
DSC differential scanning calorimetry
DVS dynamic vapor sorption
ES electrospray ionization
EtOH ethanol
FRET Forster resonance energy transfer
h hour
$H_2SO_4$ sulfuric acid
HAT histone acetyl transferase
HATU 2-(3H-[1,2,3]triazolo[4,5-b]pyridin-3-yl)-1,1,3,3-tetramethylisouronium hexafluorophosphate
HCl hydrochloric acid
Hex hexanes
HPLC high performance liquid chromatography
HTRF high-throughput time resolved FRET
$IC_{50}$ half-maximal inhibitory concentration
L liter
LCMS liquid chromatography/mass spectrometry
M molar
mL milliliter
mmol millimole
mg milligram
MHz megahertz
MS mass spectrometry
m/z mass/charge ratio
$NH_4Cl$ ammonium chloride
nm nanometer
NMR nuclear magnetic resonance
p300 EP300 (also known as KAT3B)
ppm parts per million
TGA thermogravimetric analysis
UPLC ultra performance liquid chromatography
UV ultraviolet
XRPD X-ray powder diffraction
$ZnI_2$ zinc iodide The term "organic solvent" will be readily known those skilled in the art, but may include chemical solvents such as acetone, acetonitrile, benzene, chloroform, 1,4-dioxane, diethyl ether, dichloromethane, dimethylacetamide, N,N-dimethylformamide, dimethylsulfoxide, ethanol, ethyl acetate, hexanes, isopropanol, methanol, N-methylpyrolidone, pyridine, tetrahydrofuran, toluene, water, in addition to those not explicitly named.

Example 1—Preparation of Compounds, Solid Forms, and Salts

Example 1.a—Preparation of Amorphous, Free Base+Form (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid (1)

(1R,3R)-3-[(7S)-2-[(S)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid (1')

Synthesis of intermediate
2-(5-fluoro-2-methoxyphenyl)-2-hydroxyacetic acid
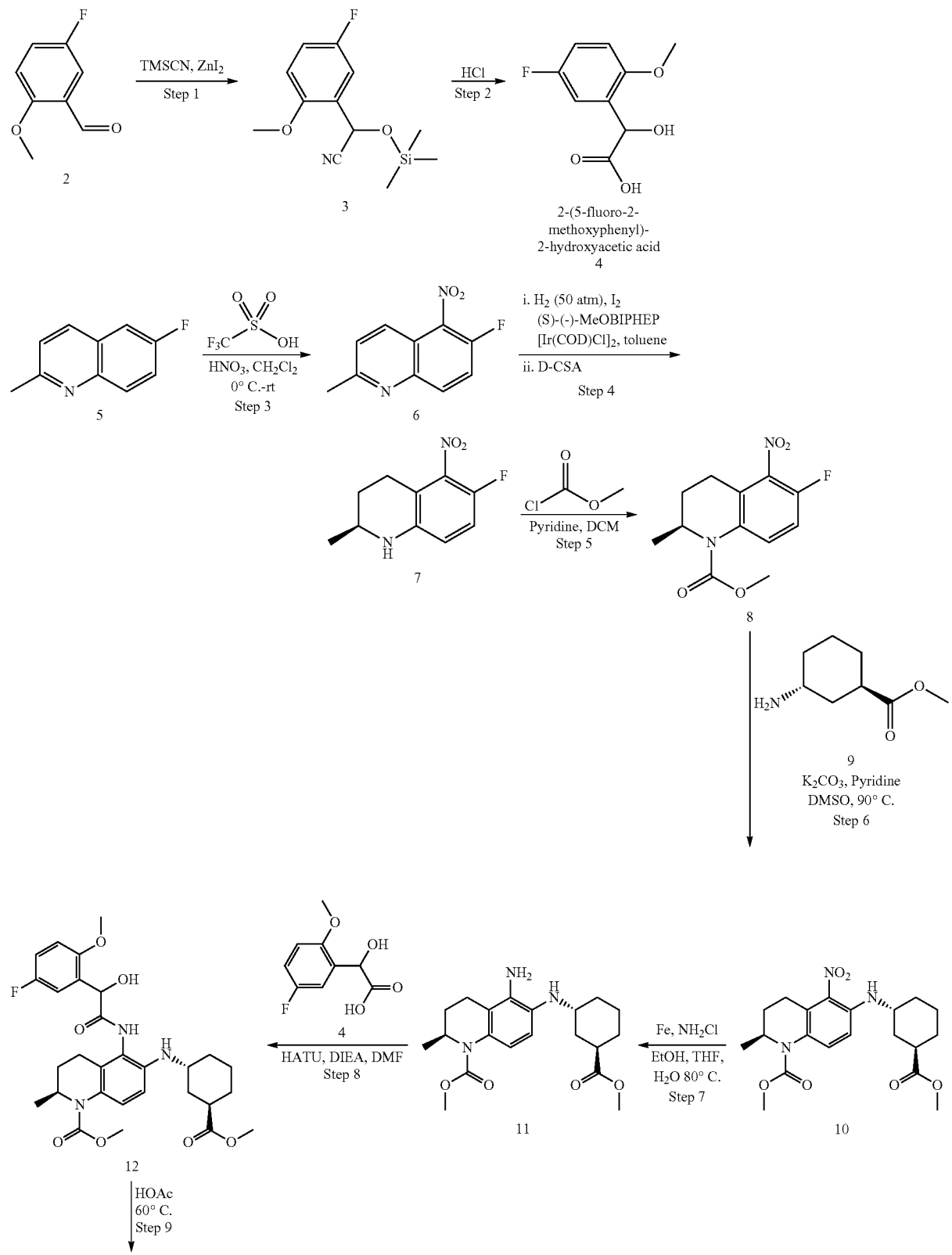

-continued

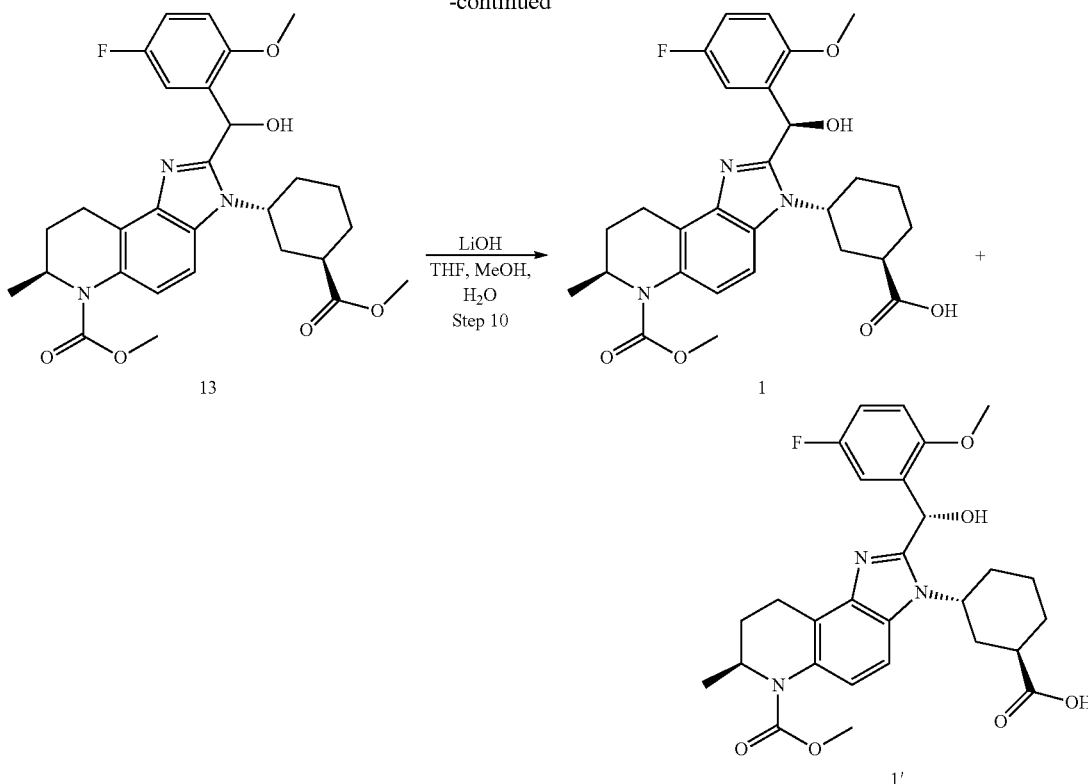

Step 1. 2-(5-fluoro-2-methoxyphenyl)-2-[(trimethylsilyl)oxy]acetonitrile

A solution of ZnI$_2$ (1.6 mg, 0.01 mmol), 5-fluoro-2-methoxybenzaldehyde (1.54 g, 9.99 mmol) in trimethylsilanecarbonitrile (1.5 mL, 11.25 mmol) was stirred for 1 h at room temperature. The resulting mixture was concentrated under vacuum. The resulting crude product was purified by silica gel chromatography (eluting with 1:1 ethyl acetate/petroleum ether) to afford 2-(5-fluoro-2-methoxyphenyl)-2-[(trimethylsilyl)oxy]acetonitrile as a white solid (2.0 g, 79%).

Step 2. 2-(5-fluoro-2-methoxyphenyl)-2-hydroxyacetic acid

A solution of 2-(5-fluoro-2-methoxyphenyl)-2-[(trimethylsilyl)oxy]acetonitrile (1.50 g, 5.92 mmol) in hydrochloric acid (10 mL, 12M). The resulting solution was stirred for 1 h at 25° C., and then stirred for 2 h at 70° C. The reaction mixture was cooled and concentrated under vacuum. The crude product was purified by reverse phase chromatography (Column: C18; Mobile phase, A: water (containing 0.05% TFA) and B: ACN (5% to 20% over 30 min); Detector, UV 254 nm) to afford 2-(5-fluoro-2-methoxyphenyl)-2-hydroxyacetic acid as a white solid (1.10 g, 93%).

Step 3. 6-fluoro-2-methyl-5-nitroquinoline

A solution of trifluoromethanesulfonic acid (82.0 mL, 0.923 mol) in HNO$_3$ (19.6 mL, 0.437 mol) was stirred for 20 min at 0° C. This was followed by the addition of 6-fluoro-2-methylquinoline (50.0 g, 0.310 mol) in dichloromethane (300 mL) at 0° C. The resulting mixture was stirred for 15 h at room temperature (25° C.). The reaction mixture was diluted with water (300 mL). The pH value of the solution was adjusted to 8 with sodium bicarbonate (saturated aqueous solution). The resulting solution was extracted with dichloromethane (3×300 mL). The combined organic layers were dried over anhydrous sodium sulfate, filtered, and concentrated under vacuum. The residue was purified by silica gel chromatography (eluting with 1:4 ethyl acetate/petroleum ether) to afford 6-fluoro-2-methyl-5-nitroquinoline as a light yellow solid (60.0 g, 94%). LCMS (ES, m/z): 207 [M+H]$^+$.

Step 4. (2S)-6-fluoro-2-methyl-5-nitro-1,2,3,4-tetrahydroquinoline

A solution of (S)-(−)-MeO-BIPHEP (1.03 g, 1.77 mmol), chloro(1,5-cyclooctadiene)iridium(I) dimer (538 mg, 0.80 mmol) in toluene (100 mL) was stirred for 30 min at room temperature (25° C.) under an atmosphere of nitrogen. This was followed by the addition of I$_2$ (410 mg, 1.62 mmol), 6-fluoro-2-methyl-5-nitroquinoline (33.0 g, 0.160 mol) in toluene (100 mL). The resulting mixture was stirred for 20 h at room temperature (25° C.) under hydrogen (50 atm). The resulting mixture was concentrated under vacuum and purified by silica gel chromatography (eluting with 1:1 ethyl acetate/petroleum ether) to afford the crude product (35.0 g). The crude product was dissolved in ethyl acetate (230 mL), followed by the addition of D-Camphorsulfonic acid (36.9 g, 0.158 mol). The resulting solution was stirred for 1 h at 60° C. and then cooled to room temperature. The solids were collected by filtration, and rinsed with ethyl acetate (120 mL). The solids were dissolved in water (50 mL). The pH value of the solution was adjusted to 8 with sodium bicarbonate (saturated aqueous solution). The resulting solution was extracted with ethyl acetate (3×120 mL). The combined organic layers were dried over anhydrous sodium sulfate, filtered, and concentrated under vacuum to afford (2S)-6-fluoro-2-methyl-5-nitro-1,2,3,4-tetrahydroquinoline as a red solid (25.5 g, 76%). LCMS (ES, m/z): 211 [M+H]$^+$.

Step 5. methyl (2S)-6-fluoro-2-methyl-5-nitro-1,2,3, 4-tetrahydroquinoline-1-carboxylate A solution of (2S)-6-fluoro-2-methyl-5-nitro-1,2,3,4-tetrahydroquinoline (25.3 g, 0.120 mol), pyridine (39.0 mL, 0.484 mol), methyl carbonochloridate (18.7 mL, 0.242 mol) in dichloromethane (150 mL) was stirred for 3 h at room temperature (25° C.). The reaction was washed with 1M hydrochloric acid (2×70 mL). The combined organic layers were dried over anhydrous sodium sulfate, filtered, and concentrated under vacuum to afford methyl (2S)-6-fluoro-2-methyl-5-nitro-1,2,3,4-tetrahydroquinoline-1-carboxylate as a yellow solid (29.8 g, 92%). LCMS (ES, m/z): 269 [M+H]$^+$.

Step 6. methyl (2S)-6-[[(1R,3R)-3-(methoxycarbonyl)cyclohexyl]amino]-2-methyl-5-nitro-1,2,3,4-tetrahydroquinoline-1-carboxylate A solution of methyl (2S)-6-fluoro-2-methyl-5-nitro-1,2, 3,4-tetrahydroquinoline-1-carboxylate (29.6 g, 0.110 mol), pyridine (29.6 mL, 0.368 mol), potassium carbonate (30.5 g, 0.220 mol), methyl (1R,3R)-3-aminocyclohexane-1-carboxylate (25.6 g, 162.84 mmol) in DMSO (270 mL) was stirred for 15 h at 90° C. and then cooled to room temperature. The reaction was quenched by the addition of water (200 mL) and extracted with ethyl acetate (3×300 mL). The combined organic layers were dried over anhydrous sodium sulfate, filtered, and concentrated under vacuum. The resulting crude product was purified by silica gel chromatography (eluting with 1:1 ethyl acetate/petroleum ether) to afford methyl (2S)-6-[[(1R,3R)-3-(methoxycarbonyl)cyclohexyl] amino]-2-methyl-5-nitro-1,2,3,4-tetrahydroquinoline-1-carboxylate as a red oil (32 g, 72%). LCMS (ES, m/z): 406 [M+H]$^+$.

Step 7. methyl (2S)-5-amino-6-[[(1R,3R)-3-(methoxycarbonyl)cyclohexyl]amino]-2-methyl-1,2, 3,4-tetrahydroquinoline-1-carboxylate A solution of methyl (2S)-6-[[(1R,3R)-3-(methoxycarbonyl)cyclohexyl]amino]-2-methyl-5-nitro-1,2,3,4-tetrahydroquinoline-1-carboxylate (31.0 g, 76.46 mmol), NH$_4$Cl (24.3 g, 454.28 mmol), Fe (64.3 g, 1.15 mol) in tetrahydrofuran (300 mL), ethanol (300 mL), water (100 mL) was stirred for 1 h at 80° C. and then cooled to room temperature. The solids were filtered out by filtration. The resulting solution was diluted with water (300 mL) and extracted with ethyl acetate (3×400 mL). The combined organic layers were dried over anhydrous sodium sulfate, filtered, and concentrated under vacuum to afford methyl (2S)-5-amino-6-[[(1R,3R)-3-(methoxycarbonyl)cyclohexyl]amino]-2-methyl-1,2,3,4-tetrahydroquinoline-1-carboxylate as a dark green solid (27.5 g, 92%). LCMS (ES, m/z): 376 [M+H]$^+$.

Step 8. methyl (2S)-5-[2-(5-fluoro-2-methoxyphenyl)-2-hydroxyacetamido]-6-[[(1R,3R)-3-(methoxycarbonyl)cyclohexyl]amino]-2-methyl-1,2,3,4-tetrahydroquinoline-1-carboxylate A solution of 2-(5-fluoro-2-methoxyphenyl)-2-hydroxyacetic acid (240 mg, 1.20 mmol), HATU (228 mg, 0.60 mmol), methyl (2S)-5-amino-6-[[(1R,3R)-3-(methoxycarbonyl)cyclohexyl]amino]-2-methyl-1,2,3,4-tetrahydroquinoline-1-carboxylate (150 mg, 0.40 mmol), DIEA (0.19 mL, 1.20 mmol) in N,N-dimethylformamide (10 mL) was stirred for 1 h at 25° C. The resulting solution was diluted with H$_2$O (10 mL). The resulting solution was extracted with ethyl acetate (3×15 mL) and the organic layers combined. The resulting mixture was washed with brine (2×20 mL). The mixture was dried over anhydrous sodium sulfate and concentrated under vacuum. The resulting crude product was purified by silica gel chromatography (eluting with 3:2 ethyl acetate/petroleum ether) to afford methyl (2S)-5-[2-(5-fluoro-2-methoxyphenyl)-2-hydroxyacetamido]-6-[[(1R, 3R)-3-(methoxycarbonyl)cyclohexyl]amino]-2-methyl-1,2, 3,4-tetrahydroquinoline-1-carboxylate as a yellow solid (180 mg, 81%). LCMS (ES, m/z): 558 [M+H]$^+$.

Step 9. methyl (7S)-2-[(5-fluoro-2-methoxyphenyl) (hydroxy)methyl]-3-[(1R,3R)-3-(methoxycarbonyl) cyclohexyl]-7-methyl-3H,6H,7H,8H,9H-imidazo[4, 5-f]quinoline-6-carboxylate A solution of methyl (2S)-5-[2-(5-fluoro-2-methoxyphenyl)-2-hydroxyacetamido]-6-[[(1R,3R)-3-(methoxycarbonyl)cyclohexyl]amino]-2-methyl-1,2,3,4-tetrahydroquinoline-1-carboxylate (180 mg, 0.32 mmol) in AcOH (8 mL) was stirred for overnight at 60° C. The reaction mixture was cooled and concentrated under vacuum. The resulting crude product was purified by silica gel chromatography (eluting with 1:1 ethyl acetate/petroleum ether) to afford methyl (7S)-2-[(5-fluoro-2-methoxyphenyl)(hydroxy)methyl]-3-[(1R,3R)-3-(methoxycarbonyl)cyclohexyl]-7-methyl-3H, 6H,7H,8H, 9H-imidazo[4,5-f]quinoline-6-carboxylate as a yellow solid (120 mg, 69%). LCMS (ES, m/z): 540 [M+H]$^+$.

Step 10. (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid; (1R,3R)-3-[(7S)-2-[(S)-(5-fluoro-2-methoxyphenyl)(hydroxy) methyl]-6-(methoxycarbonyl)-7-methyl-3H,6H,7H, 8H,9H-imidazo[4,5-f]quinolin-3-yl]cyclohexane-1-carboxylic acid A solution of methyl (7S)-2-[(5-fluoro-2-methoxyphenyl) (hydroxy)methyl]-3-[(1R,3R)-3-(methoxycarbonyl)cyclohexyl]-7-methyl-3H,6H,7H,8H,9H-imidazo[4,5-f]quinoline-6-carboxylate (120 mg, 0.22 mmol), and LiOH (16 mg, 0.67 mmol) in tetrahydrofuran (2.0 mL), methanol (2.0 mL) and water (2.0 mL) was stirred overnight at 25° C. The resulting mixture was concentrated under vacuum. The crude product was purified by Prep-HPLC (Column, XBridge Prep C18 OBD Column, 19×150 mm, Sum; Mobile phase, A: water (containing 10 mmol/L NH$_4$HCO$_3$) and B: ACN (15.0% to 29.0% over 14 min); Detector, UV 220/254 nm). The product was separated by Chiral-Prep-HPLC (Column, CHIRALPAK IE, 2×25 cm, 5 um; Mobile phase, A: Hex (containing 0.1% FA) and B: ethanol (hold 50.0% ethanol over 12 min); Detector, UV 220/254 nm). The product fractions were concentrated to afford (1R,3R)-3-[(7S)-2-[(R)-(5-fluoro-2-methoxyphenyl)(hydroxy)methyl]-6-(methoxycarbonyl)-7-methyl-3H,6H,7H,8H,9H-imidazo [4,5-f]quinolin-3-yl]cyclohexane-1-carboxylic acid as a white solid (23.6 mg, 20%); and (1R,3R)-3-[(7S)-2-[(S)-(5-fluoro-2-methoxyphenyl)(hydroxy)methyl]-6-(methoxycarbonyl)-7-methyl-3H,6H,7H,8H,9H-imidazo[4,5-f]quinolin-3-yl]cyclohexane-1-carboxylic acid as a white solid (23.8 mg, 20%). Stereoisomeric purity was determined via HPLC: Column: CHIRALPAK IE-3, Column size: 0.46×5 cm; 3 μm; Mobile phase: Hex (0.1% FA):EtOH=50:50, Flow: 1.0 ml/min. Compound purity was assessed at greater than 99%, as determined by HPLC analysis.

First eluting isomer (1): $^1$H-NMR (CD$_3$OD, 400 MHz) δ (ppm): 7.56-7.47 (m, 1H), 7.47-7.31 (m, 1H), 7.21-7.09 (m, 1H), 7.09-6.89 (m, 2H), 6.53 (s, 1H), 4.81-4.61 (m, 2H), 3.85 (s, 3H), 3.78 (s, 3H), 3.31-3.18 (m, 1H), 3.06-2.82 (m, 2H), 2.57-2.41 (m, 1H), 2.41-2.31 (m, 1H), 2.31-2.09 (m, 3H), 1.83-1.58 (m, 3H), 1.49-1.21 (m, 2H), 1.16 (d, J=6.8 Hz, 3H). LCMS (ES, m/z): 526 [M+H]$^+$.

Second eluting isomer (1'): $^1$H-NMR (CD$_3$OD, 400 MHz) δ (ppm): 7.69-7.44 (m, 2H), 7.44-7.29 (m, 1H), 7.12-6.99 (m, 1H), 6.98-6.82 (m, 1H), 6.37 (s, 1H), 5.03-4.91 (m, 1H), 4.81-4.69 (m, 1H), 3.78 (s, 3H), 3.61 (s, 3H), 3.22-3.04 (m, 1H), 3.02-2.87 (m, 2H), 2.54-2.41 (m, 1H), 2.41-2.27 (m, 1H), 2.27-2.08 (m, 3H), 1.82-1.58 (m, 3H), 1.58-1.41 (m, 2H), 1.14 (d, J=6.4 Hz, 3H). LCMS (ES, m/z): 526 [M+H]$^+$.

Example 1.b—Preparation of Hydrochloric Acid Addition Salt Type A 900 mg of (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid was dissolved in 16.5 mL of ethyl acetate and 37% hydrochloric acid was added in 3 aliquots (57 uL each) with vigorous stirring. Solids precipitate and redissolve after the first two aliquots but the third addition has solids persist. The slurry is stirred in 50° C. oil bath for two hours and is then slowly cooled to ambient temperature over night. The white slurry was cooled in ice bath for 90 minutes and filtered/washed with cold ethyl acetate. The white solids were air dried to 908 mg (94% yield). LCMS (ES, m/z): 526 [M+H]$^+$ The samples were further characterized by XRPD, DSC and TGA. The results indicated that the sample is crystalline by XRPD and conformed to HCL Salt Type A.

Example 1.c—Preparation of Hydrochloric Acid Addition Salt: Type B 20 mg of the type A hydrochloric acid addition salt of (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid was dissolved in 0.4 mL of a 1:1 mixture of dichloromethane and isopropanol. The solution was heated to 50° C., subsequently cooled to 5° C. at a rate of 0.1° C. per minute, and then stirred at 5° C. overnight. The solution was then warmed to room temperature and a precipitate was observed following the slow, unassisted evaporation of a portion of the solvent. The precipitate was collected via centrifugation, dried at 40° C. under vacuum, and subsequently characterized by XRPD, DSC, and TGA. The results indicated that the sample is crystalline via XRPD and conformed to the type B hydrochloric acid addition salt.

Example 1.d—Preparation of Hydrochloric Acid Addition Salt: Type C 20 mg of the type A hydrochloric acid addition salt of (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid was dissolved in 0.4 mL of a 9:1 mixture of 1,4-dioxane and water. The solution was heated to 50° C., subsequently cooled to 5° C. at a rate of 0.1° C. per minute, and then stirred at 5° C. overnight. The solution was then warmed to room temperature and a precipitate was observed following the slow, unassisted evaporation of a portion of the solvent. The precipitate was collected via centrifugation, dried at 40° C. under vacuum, and subsequently characterized by XRPD, DSC, and TGA. The results indicated that the sample is crystalline via XRPD and conformed to the type C hydrochloric acid addition salt.

Example 1.e—Preparation of p-Toluenesulfonic Acid Addition Salt: Type A 20 mg of (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid was dissolved in 0.4 mL ethyl acetate and mixed with 1 equivalent of p-toluenesulfonic acid. The resulting solution was stirred at room temperature for 3 days. The resulting solid was collected via centrifugation, dried at 40° C. under vacuum, and subsequently characterized by XRPD, DSC, TGA, and $^1$H NMR. The results indicated that the sample is crystalline via XRPD and conformed to the type A p-toluenesulfonic acid addition salt.

Example 1.f—Preparation of p-Toluenesulfonic Acid Addition Salt: Type B 300.6 mg of (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid was dissolved in 4.0 mL of acetonitrile in a 20 mL vial to form a suspension. 107.34 mg of p-toluenesulfonic acid was dissolved in 1.5 mL of acetonitrile and added to the suspension slowly. The suspension was then heated to 50° C. and subsequently cooled to 5° C. at a rate of 0.1° C. per minute. After stirring at 5° C. overnight, the resulting precipitate was collected via centrifugation and dried at 40° C. under vacuum to yield 231.8 mg of white powder. The solid was characterized via XRPD, DSC, TGA, and NMR and the results indicated that the sample is crystalline via XRPD and conformed to the type B p-toluenesulfonic acid addition salt.

Example 1.g—Preparation of Benzenesulfonic Acid Addition Salt: Type A 20 mg of (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid was dissolved in 0.4 mL ethyl acetate and mixed with 1 equivalent of benzenesulfonic acid. The resulting solution was stirred at room temperature for 3 days. After no precipitation was observed at the three day mark, the solution was heated to 50° C. and slowly cooled to 5° C. at a rate of 0.1° C. per minute. A solid precipitate was observed after stirring the solution at 5° C. overnight. The resulting solid was collected via centrifugation, dried at 40° C. under vacuum, and subsequently characterized by XRPD, DSC, TGA, and $^1$H NMR. The results indicated that the sample is crystalline via XRPD and conformed to the type A benzenesulfonic acid addition salt.

Example 1.h—Preparation of Sulfuric Acid Addition Salt: Type A 20 mg of (1R,3R)-3-((S)-2-((R)-(5-fluoro-2-methoxyphenyl)(hydroxy)methyl)-6-(methoxycarbonyl)-7-methyl-6,7, 8,9-tetrahydro-3H-imidazo[4,5-f]quinolin-3-yl)cyclohexane-1-carboxylic acid was dissolved in 0.4 mL ethyl acetate and mixed with 1 equivalent of sulfuric acid. The resulting solution was stirred at room temperature for 3 days. After no precipitation was observed at the three day mark, the solution was heated to 50° C. and slowly cooled to 5° C. at a rate of 0.1° C. per minute. A solid precipitate was observed after stirring the solution at 5° C. overnight. The resulting solid was collected via centrifugation, dried at 40° C. under vacuum, and subsequently characterized by XRPD, DSC, and TGA. The results indicated that the sample is crystalline via XRPD and conformed to the type A sulfuric acid addition salt.

Example 1.i—Preparation of Crystalline Freeform Type A

The (1R,3R)-3-((S)-2-((R)-(5-fluoro-2-methoxyphenyl)(hydroxy)methyl)-6-(methoxy-carbonyl)-7-methyl-6,7,8,9-tetrahydro-3H-imidazo[4,5-f]quinolin-3-yl)cyclohexane-1-carboxylic acid (5.00 g, 9.51 mmol) was completely dissolved in hot ethyl acetate (67 mL) at reflux. Cloudiness occurs after briefly cooling over several minutes. The hot slurry cooled slowly to ambient temperature and was then stirred for 1 h. The slurry was then cooled to 0° C. and stirred for 2 h in ice bath before filtering and washing solids with cold ethyl acetate. Isolation gave 3.70 g (74% recovery), white powder of increased purity after drying. LCMS (ES, m/z): 526 [M+H]$^+$. The samples were further characterized by XRPD, DSC, and TGA. These results indicated that the sample is crystalline by XRPD and conformed to Freeform Type A.

Example 2—Kinetic Solubility Assessments

Solubility of HCl salt Type A, tosylate Type B, and freeform type A was measured in water, SGF, FaSSIF and FeSSIF at 37° C. with solid loading of ~10 mg/mL calculated as freebase. All solubility samples were kept rolling at 25 rpm at 37° C., and sampled at 1, 4, and 24 h, respectively. Supernatant was extracted via centrifugation before filtration, and used for solubility and pH measurement. Residual solids were collected for XRPD characterization. The results are summarized in FIG. 7.

Example 3—HTRF Biochemical Assay for CBP and BRD4 Activity

The ability of amorphous Compound 1 to selectively inhibit CBP was determined using the following HTRF biochemical assay for CBP and BRD4 activity. Compound 2 was used as a reference compound:

The assay was performed in a final volume of 6 μL in assay buffer containing 50 mM Hepes (pH 7.5, (0.5M Hepes, pH 7.5 solution; Teknova H1575)), 0.5 mM GSH, 0.01% BGG (0.22 μM filtered, Sigma, G7516-25G), 0.005% BSA (0.22 μM filtered, EMD Millipore Corporation, 126575) and 0.01% Triton X-100 (Sigma, T9284-10L). Nanoliter quantities of 10-point, 3-fold serial dilution in DMSO were pre-dispensed into 1536 assay plates (Corning, #3724BC) for a final test concentration of 33 μM to 1.7 nM, top to lowest dose, respectively. 3 μL of 2× Protein and 3 μL of 2× Peptide Ligand were added to assay plates (pre-stamped with compound). Plates were incubated for varying times at room temperature prior to measuring the signal. TR-FRET (Time-Resolved Fluorescence Resonance Energy Transfer) was measured on a PHERAstar plate reader (BMG, equipped with HTRF optic module [337/520/490]) or on an Envision plate reader (PerkinElmer, equipped with the TRF Laser unit, TRF dual mirror D400/D505 and emission filters M520 and M495). Data were reported as percent inhibition compared with control wells based on the following equation: % inh=1−((TR-FRET ratio−AveLow)/(AveHigh−AveLow)) where TR-FRET ratio=(Fluorescence at 520 nm/Fluorescence at 490 nm)*10000), AveLow=average TR-FRET ratio of no enzyme control (n=32), and AveHigh=average TR-FRET ratio of DMSO control (n=32). IC50 values were determined by curve fitting of the standard 4 parameter logistic fitting algorithm included in the Activity Base software package: IDBS XE Designer Model205. Data is fitted using the Levenburg Marquardt algorithm. For all assay formats data were reported as percent inhibition compared with control wells based on the following equation: % inh=100*((FLU−AveLow)/(AveHigh−AveLow)) where FLU=measured Fluorescence, AveLow=average Fluorescence of no enzyme control (n=32), and AveHigh=average Fluorescence of DMSO control (n=32). IC50 values were determined by curve fitting of the standard 4 parameter logistic fitting algorithm included in the Activity Base software package: IDBS XE Designer Model205. Data is fitted using the Levenburg Marquardt algorithm. An IC$_{50}$ measurement for Compound 1 of between 0.001 and 0.01 μM for the inhibition of CBP, and between 1.0 and 1000 μM for the inhibition of BRD4 was observed. An IC$_{50}$ measurement for Compound 2 of between 0.001 and 0.01 μM for the inhibition of CBP, and between 1.0 and 1000 μM for the inhibition of BRD4 was observed.

Example 4—Compound 1 and Compound 1' Demonstrated In Vitro Activity Against CBP

The potency and selectivity of CBP/P300 inhibitor compounds including Compound 1 and Compound 1':

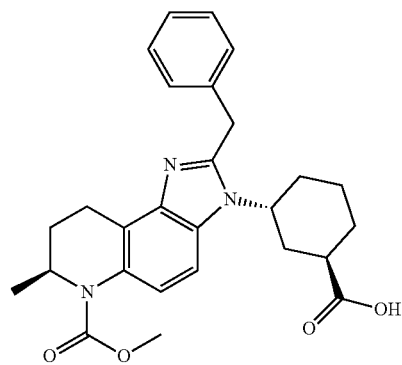

(2)

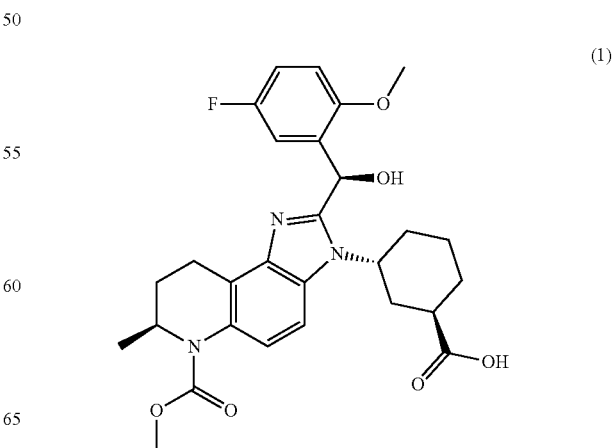

(1)

-continued

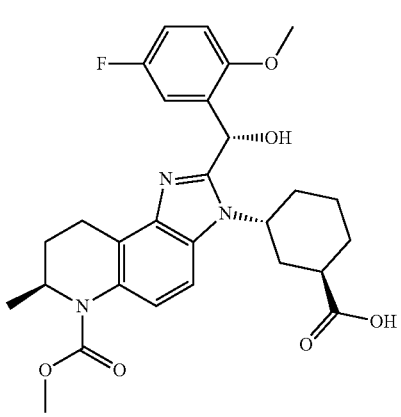
(1')

were determined in biochemical time resolved fluorescence assays using GST fusions of the bromodomains of CBP and BRD4. Briefly, CBP inhibitors were pre-dispensed into 1536 assay plates for a final test concentration of 33 μM to 1.7 nM. Protein and Ligands were added to the compound to a final concentration of 2.5 nM CBP or BRD4 (N-terminal GST-CREBBP (1081-1197), BRD4 tandem domains) and 25 nM Tetra-Acetylated H3 peptide Plates and incubated for 4 h. Data were reported as percent inhibition compared with control wells. $IC_{50}$ values were determined by curve fitting of the standard 4 parameter logistic fitting algorithm. In these conditions, Compound 1 was determined to be a potent inhibitor of CBP with an $IC_{50}$<2 nM (N=16). In a similar assay, BRD4 potency was determined and Compound 1 showed an $IC_{50}$ of <500 nM (N=15), indicating >200-fold selectivity.

Selectivity of Compound 1 was evaluated in screening assays for kinase inhibition and BRD binding. Compound 1 showed no to low binding affinity for the human kinases and disease-relevant mutant variants evaluated in a KINOMEscan™ screen. A panel of 10 BRD representing the various branches or the bromodomain tree were tested using an AlphaScreen. Of the 10 bromodomains surveyed, Compound 1 was inactive against 8. Compound 1 $IC_{50}$ values for bromodomains of CREBBP and BRD4 (tandem BD1/BD2) were 0.1 and >10 μM, respectively, confirming the high selectivity of Compound 1 for CBP.

The ability of Compound 1 and Compound 1' to selectively inhibit CBP was determined using the biochemical assay of Example 3 for CBP and BRD4 activity. Results are shown in the table below:

| Compound | CBP ($IC_{50}$) | Selectivity Ratio of BRD4 ($IC_{50}$)/CBP ($IC_{50}$) |
|---|---|---|
| 1 | <10 nM | >240 |
| 1' | <20 nM | >76 |

Both Compound 1 and Compound 1' potently inhibited (e.g., $IC_{50}$<100 nM) CBP in the HTRF biochemical assay of Example 3, while Compound 1 was about 3.5-times more selective for CBP inhibition compared to BRD4 using this assay.

Example 5—Compositions Including Compound 1

Pharmaceutical compositions including Compound 1 were prepared in a capsule form by blending milled and micronized Compound 1 with excipients (e.g. fillers, disintegrants, surfactants, glidants, and lubricants), followed by encapsulation. Capsules including dose strengths of 25 mg and 100 mg of the Type A hydrochloric acid addition salt of Compound 1, equivalent to the free base form of Compound 1, were prepared.

The final blends were filled into suitable size white, opaque capsule shells to prepare the 25 mg and 100 mg dose strength capsules.

The compositions of the 25 mg and 100 mg dose strength capsules are summarized in Tables 1 and 2, below.

TABLE 1

100 mg Dose Strength Composition Including Compound 1

| Component | % Composition | Unit Weight, mg |
|---|---|---|
| Micronized Compound 1 (Type A HCl addition salt) | 36.57 | 109.72 |
| Avicel PH 101 | 27.71 | 83.14 |
| Mannitol M200 | 27.71 | 83.14 |
| Sodium Lauryl Sulfate | 1.50 | 4.50 |
| Ac-Di-Sol | 5.00 | 15.00 |
| Fumed Silica | 1.00 | 3.00 |
| Magnesium Stearate | 0.50 | 1.50 |
| Total | 100.00 | 300.00 |

TABLE 2

25 mg Dose Strength Composition Including Compound 1

| Component | % Composition | Unit Weight, mg |
|---|---|---|
| Micronized Compound 1 (Type A HCl addition salt) | 10.97 | 27.43 |
| Avicel PH 101 | 40.51 | 101.28 |
| Mannitol M200 | 40.51 | 101.28 |
| Sodium Lauryl Sulfate | 1.50 | 3.75 |
| Ac-Di-Sol | 5.00 | 12.50 |
| Fumed Silica | 1.00 | 2.50 |
| Magnesium Stearate | 0.50 | 1.25 |
| Total | 100.00 | 250.00 |

Example 6—Granulated Compositions Including Compound 1

Pharmaceutical compositions including Compound 1 were prepared in a capsule form by first preparing a common, intragranular blend for a 100 mg dose strength of the Type A hydrochloric acid addition salt, equivalent to the free base form of Compound 1. Preparation of the common blend included blending micronized Compound 1 with intragranular excipients (e.g. fillers, disintegrants, surfactants, glidants, and lubricants), followed milling, and then compaction.

Aliquots of the common intragranular blend were then blended with extragranular excipients (e.g. fillers, disintegrants, glidants, and lubricants) to achieve the desired final blends for encapsulation with dose strengths of 25 mg and 100 mg, equivalent to the free base form of Compound 1.

The final granulations were filled into suitable size white, opaque capsule shells to prepare the 25 mg and 100 mg dose strength capsules.

The composition of the common, intragranular blend is summarized in Table 3, below. The compositions of the 25 mg and 100 mg dose strength capsules are summarized in Tables 4 and 5, below.

TABLE 3

Common Blend (Intragranular Blend)

| Component | % Composition | Unit Weight, mg |
|---|---|---|
| Micronized Compound 1 (Type A HCl addition salt) | 33.76 | 109.72 |
| Avicel PH102 | 42.74 | 138.91 |
| Mannitol M200 | 15.00 | 48.75 |
| Kollidon CL | 5.00 | 16.25 |
| Fumed Silica | 1.00 | 3.25 |
| Sodium Lauryl Sulfate | 1.50 | 4.88 |
| Total Intragranular Material | 99.0 | 321.75 |

TABLE 4

100 mg Dose Strength Granulated Composition Including Compound 1

| Component | % Composition | Unit Weight, mg |
|---|---|---|
| Intragranular Blend | 99.00 | 321.75 |
| Fumed Silica | 0.50 | 1.63 |
| Magnesium Stearate | 0.50 | 1.63 |
| Total | 100.00 | 325.00 |

TABLE 5

25 mg Dose Strength Granulated Composition Including Compound 1

| Component | % Composition | Unit Weight, mg |
|---|---|---|
| Intragranular Blend | 26.81 | 80.44 |
| Avicel PH 200 | 72.19 | 216.56 |
| Fumed Silica | 0.50 | 1.50 |
| Magnesium Stearate | 0.50 | 1.50 |
| Total | 100.00 | 300.00 |

Further embodiments of the disclosure are set out in the following numbered embodiments:

1. A non-amorphous, solid form of a compound of formula (I):

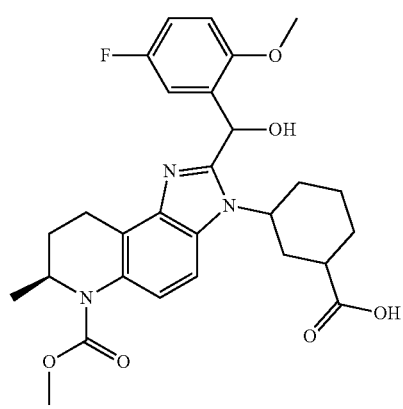

(I)

and salts thereof.

2. The solid form of embodiment 1, wherein the compounds have the stereochemistry of formula

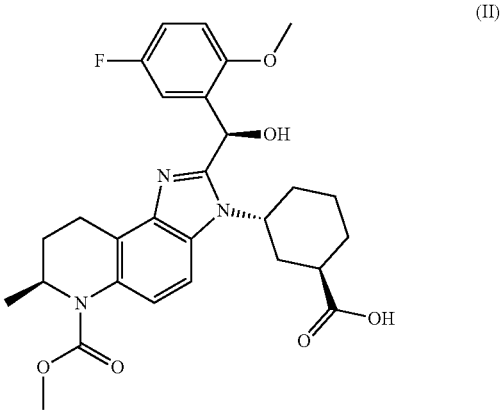 [SMILES: COC(=O)N1c2ccc3c(nc([C@H](O)c4cc(F)ccc4OC)n3[C@@H]3CCC[C@@H](C(=O)O)C3)c2CC[C@@H]1C]

(II)

and salts thereof.

3. The solid form of any one of embodiment 1 and 2, wherein the salt is an acid addition salt selected from: hydrochloric acid, p-toluenesulfonic acid, benzenesulfonic acid, and sulfuric acid.

4. The solid form of embodiment 3, wherein the salt is a hydrochloric acid addition salt.

5. The solid form of embodiment 4, wherein the hydrochloric acid addition salt form is type A characterized by an X-ray powder diffraction pattern comprising at least three peak positions (degrees 2θ±0.2) when measured using Cu Kα radiation, selected from the group consisting of: 7.27, 8.98, 10.60, 15.60, and 23.93.

6. The solid form of embodiment 4, wherein the hydrochloric acid addition salt form is type B characterized by an X-ray powder diffraction pattern comprising at least three peak positions (degrees 2θ±0.2) when measured using Cu Kα radiation, selected from the group consisting of: 10.23, 18.72, 23.03, 24.77, and 28.03.

7. The solid form of embodiment 4, wherein the hydrochloric acid addition salt form is type C characterized by an X-ray powder diffraction pattern comprising at least three peak positions (degrees 2θ±0.2) when measured using Cu Kα radiation, selected from the group consisting of: 7.05, 19.84, 21.09, 24.98, and 31.44.

8. The solid form of embodiment 3, wherein the salt is a p-toluenesulfonic acid addition salt.

9. The solid form of embodiment 8, wherein the p-toluenesulfonic acid addition salt form is type A characterized by an X-ray powder diffraction pattern comprising at least three peak positions (degrees 2θ±0.2) when measured using Cu Kα radiation, selected from the group consisting of: 6.59, 13.20, 14.46, 18.00, and 21.74.

10. The solid form of embodiment 8, wherein the p-toluenesulfonic acid addition salt form is type B characterized by an X-ray powder diffraction pattern comprising at least three peak positions (degrees 2θ±0.2) when measured using Cu Kα radiation, selected from the group consisting of: 7.10, 9.15, 15.08, 16.19, 17.25, 18.31, and 21.13.

11. The solid form of embodiment 3, wherein the salt is a benzenesulfonic acid addition salt.

12. The solid form of embodiment 11, wherein the benzenesulfonic acid addition salt form is type A characterized by an X-ray powder diffraction pattern comprising at least three peak positions (degrees 2θ±0.2) when measured using Cu Kα radiation, selected from the group consisting of: 5.84, 7.48, 9.45, 16.84, 18.90, 19.61, 20.70, and 25.14.

13. The solid form of embodiment 3, wherein the salt is a sulfuric acid addition salt.

14. The solid form of embodiment 13, wherein the sulfuric acid addition salt form is type A characterized by an X-ray powder diffraction pattern comprising at least three peak positions (degrees 2θ±0.2) when measured using Cu Kα radiation, selected from the group consisting of: 8.24, 9.98, 13.58, 16.87, 18.78, 20.00, and 25.52.

15. The solid form of any one of embodiment 1 and 2, wherein solid form is freeform type A characterized by an X-ray powder diffraction pattern comprising at least three peak positions (degrees 2θ±0.2) when measured using Cu Kα radiation, selected from the group consisting of: 11.11, 14.11, 18.21, 20.48, and 26.24.

16. A method for preparing the solid form of compounds of embodiment 1, comprising:

suspending a free base, amorphous compound of Formula (I) in an acidic, organic solvent or mixture of organic solvents forming a solution; heating the solution; and cooling the solution.

17. A method for preparing the solid form of compounds of embodiment 15, comprising:

suspending a free base, amorphous compound of Formula (I) in an organic solvent;

heating the solution; and cooling the solution before filtering and washing the precipitated solid material.

18. A pharmaceutical composition comprising the solid form of any one of embodiments 1-15 and one or more of a pharmaceutically acceptable carrier, adjuvant, and vehicle.

19. A method of inhibiting one or more of CBP/p300-family bromodomains in a patient comprising administering to the patient in need thereof an effective amount of the solid form of any one of embodiment 1-15, or the pharmaceutical composition of embodiment 18.

20. A method of treating, preventing, inhibiting, or eliminating a disease or disorder associated with the activity of one or more CBP/p300-family bromodomains in a patient, comprising: administering to the patient in need thereof a therapeutically effective amount of the solid form of any one of embodiment 1-15 or a composition of embodiment 18.

21. A solid form of any one of embodiments 1-15 or composition of embodiment 18 for use in the manufacture of a medicament for treating a disease associated with inhibiting one or more of CBP/p300-family bromodomains.

22. Use of a solid form of any one of embodiments 1-15 or composition of embodiment 18 in the treatment of a disease associated with inhibiting one or more of CBP/p300-family bromodomains.

Alternative embodiments of the disclosure are set out in the following numbered embodiments:

1. A solid form of a compound of formula (II):

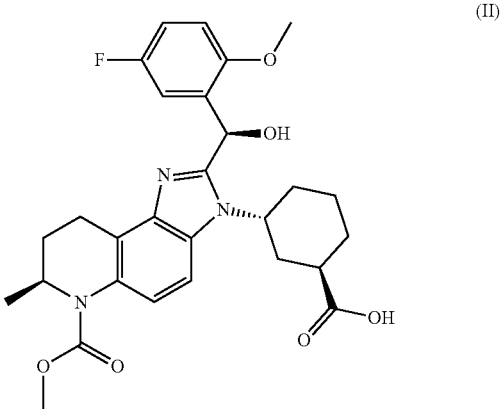

wherein the solid form is a hydrochloric acid addition salt, and wherein the hydrochloric acid addition salt is Type A hydrochloric acid addition salt.

2. The solid form of embodiment 1, wherein the solid form is characterized by an X-ray powder diffraction pattern comprising at least three peak positions (degrees 2θ±0.2) when measured using Cu Kα radiation, selected from the group consisting of: 7.27, 8.98, 10.60, 15.60, and 23.93.

3. The solid form of any one of embodiments 1 and 2, wherein the solid form is characterized by an endothermic peak having an onset temperature of about 230° C., as measured by differential scanning calorimetry.

4. The solid form of any one of embodiments 1-3, wherein the solid form is characterized by a weight loss of about 1.1% at temperatures up to 170° C., as measured by thermogravimetric analysis.

5. The solid form of any one of embodiments 1-4, wherein the solid form is an anhydrate.

6. The solid form of any one of embodiments 1-5, wherein the solid form is hygroscopic.

7. The solid form of any one of embodiments 1-6, wherein the solid form is stable for at least two weeks at temperatures up to 40° C. and relative humidity up to 75%.

8. A method for preparing a solid form of a compound of formula (II):

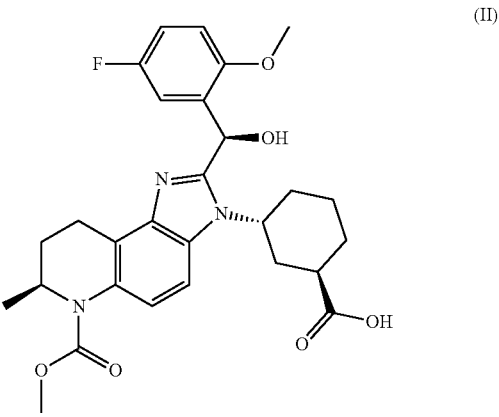 [SMILES: COC(=O)N1c2ccc3c(nc([C@H](O)c4cc(F)ccc4OC)n3[C@@H]3CCC[C@@H](C(=O)O)C3)c2CC[C@@H]1C]

comprising:
    dissolving the compound in an organic solvent, or a mixture of organic solvents to form a solution; and
    adding hydrochloric acid to the solution;
wherein the solid form is a hydrochloric acid addition salt, and wherein the hydrochloric acid addition salt is Type A hydrochloric acid addition salt.

9. The method of embodiment 8, wherein the organic solvent is ethyl acetate.

10. The method of any one of embodiments 8 and 9, wherein the hydrochloric acid is at a concentration of about 37% w/v.

11. The method of any one of embodiments 8-10, wherein the method further comprises heating the solution.

12. The method of any one of embodiments 8-11, wherein the method further comprises cooling the solution.

13. A pharmaceutical composition comprising the solid form of any one of embodiments 1-7 and one or more of a pharmaceutically acceptable carrier, adjuvant, or vehicle.

14. A pharmaceutical composition comprising the solid form of any one of embodiments 1-7, as described in Example 5.

15. A pharmaceutical composition comprising the solid form of any one of embodiments 1-7, as described in Example 6.

16. A method of inhibiting one or more CBP/p300-family bromodomains in a patient comprising administering to the patient in need thereof a therapeutically effective amount of the solid form of any one of embodiments 1-7 or the pharmaceutical composition of any one of embodiments 13-15.

17. A method of treating, preventing, inhibiting, or eliminating a disease or disorder associated with the activity of one or more CBP/p300-family bromodomains in a patient comprising administering to the patient in need thereof a therapeutically effective amount of the solid form of any one of embodiments 1-7 or the pharmaceutical composition of any one of embodiments 13-15.

Further embodiments of the disclosure are set out in the following numbered embodiments:

1. A solid form of a hydrochloric acid addition salt of a compound of formula (II):

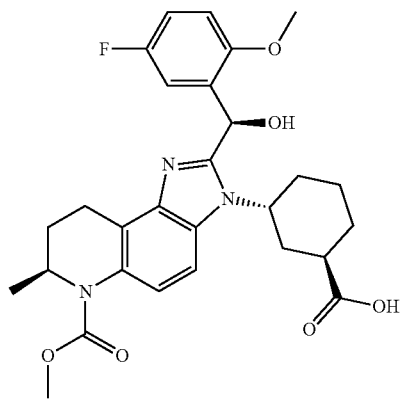

(II)

characterized by an X-ray powder diffraction pattern comprising at least three peak positions (degrees 2θ±0.2) when measured using Cu Kα radiation, selected from the group consisting of: 7.27, 8.98, 10.60, 15.60, and 23.93.

2. A solid form of a compound of formula (II):

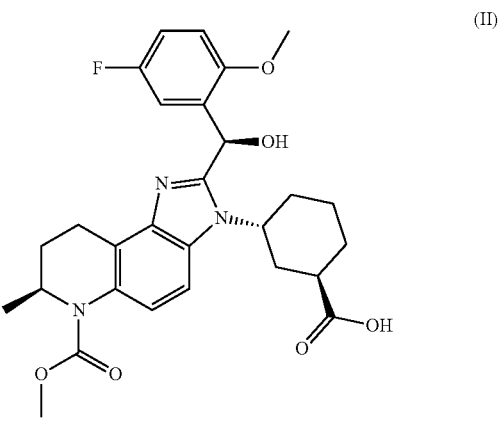 [SMILES: COC(=O)N1c2ccc3c(nc([C@H](O)c4cc(F)ccc4OC)n3[C@@H]3CCC[C@@H](C(=O)O)C3)c2CC[C@@H]1C]

(II)

wherein the solid form is a hydrochloric acid addition salt, and wherein the hydrochloric acid addition salt is Type A hydrochloric acid addition salt.

3. The solid form of embodiment 1 or embodiment 2, wherein the solid form is characterized by an endothermic peak having an onset temperature of about 230° C., as measured by differential scanning calorimetry.

4. The solid form of embodiment 1 or embodiment 2, wherein the solid form is characterized by a weight loss of about 1.1% at temperatures up to 170° C., as measured by thermogravimetric analysis.

5. The solid form of embodiment 1 or embodiment 2, wherein the solid form is an anhydrate.

6. The solid form of embodiment 1 or embodiment 2, wherein the solid form is hygroscopic.

7. The solid form of embodiment 1 or embodiment 2, wherein the solid form is stable for at least two weeks at temperatures up to 40° C. and relative humidity up to 75%.

8. A method for preparing a hydrochloric acid addition salt of a compound of formula (II):

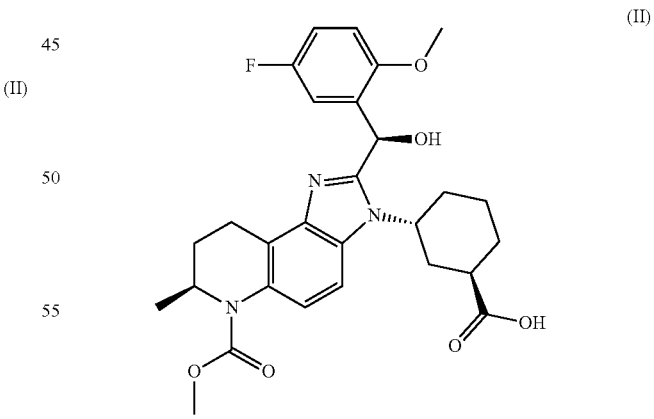

(II)

comprising:
    dissolving the compound in an organic solvent, or a mixture of organic solvents to form a solution; and
    adding hydrochloric acid to the solution;
wherein the hydrochloric acid addition salt is characterized by an X-ray powder diffraction pattern comprising at least three peak positions (degrees 2θ±0.2) when measured using Cu Kα radiation, selected from the group consisting of: 7.27, 8.98, 10.60, 15.60, and 23.93.

9. A method for preparing a solid form of a compound of formula (II):

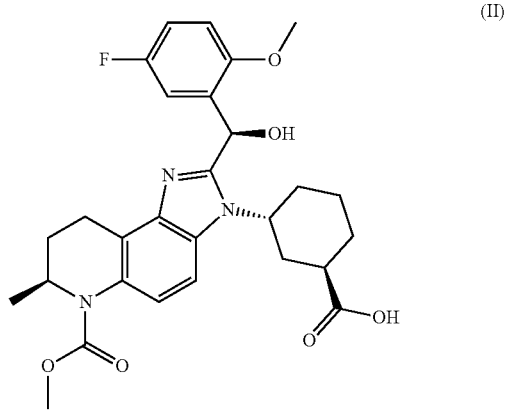 [SMILES: COC(=O)N1c2ccc3c(nc([C@H](O)c4cc(F)ccc4OC)n3[C@@H]3CCC[C@@H](C(=O)O)C3)c2CC[C@@H]1C]

(II)

comprising:
dissolving the compound in an organic solvent, or a mixture of organic solvents to form a solution; and
adding hydrochloric acid to the solution;
wherein the solid form is a hydrochloric acid addition salt, and wherein the hydrochloric acid addition salt is Type A hydrochloric acid addition salt.

10. The method of embodiment 8 or embodiment 9, wherein the organic solvent is ethyl acetate.

11. The method of embodiment 8 or embodiment 9, wherein the hydrochloric acid is at a concentration of about 37% w/v.

12. The method of embodiment 8 or embodiment 9, wherein the method further comprises heating the solution.

13. The method of embodiment 12, wherein heating the solution comprises heating the solution to a temperature of about 50° C.

14. The method of embodiment 12, wherein the method further comprises cooling the solution.

15. The method of embodiment 14, wherein cooling the solution comprises cooling the solution to a temperature of about 20° C. to about 25° C.

16. The method of embodiment 8 or embodiment 9, wherein the method further comprises filtering the solid form.

17. A pharmaceutical composition comprising the solid form of embodiment 1 or embodiment 2 and one or more of a pharmaceutically acceptable carrier, adjuvant, or vehicle.

18. A pharmaceutical composition comprising the solid form of embodiment 1 or embodiment 2, wherein the pharmaceutical composition is as described in Example 5.

19. A pharmaceutical composition comprising the solid form of embodiment 1 or embodiment 2, wherein the pharmaceutical composition is as described in Example 6.

20. A method of inhibiting one or more CBP/p300-family bromodomains in a patient comprising administering to the patient in need thereof a therapeutically effective amount of the solid form of embodiment 1 or embodiment 2.

21. A method of inhibiting one or more CBP/p300-family bromodomains in a patient comprising administering to the patient in need thereof a therapeutically effective amount of the pharmaceutical composition of any one of embodiments 17-19.

22. A method of treating breast cancer in a patient comprising administering to the patient in need thereof a therapeutically effective amount of the solid form of embodiment 1 or embodiment 2, or the pharmaceutical composition of any one of embodiments 17-19.

23. A method of treating prostate cancer in a patient comprising administering to the patient in need thereof a therapeutically effective amount of the solid form of embodiment 1 or embodiment 2, or the pharmaceutical composition of any one of embodiments 17-19.

24. A solid form of a hydrochloric acid salt of (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid, characterized by an X-ray powder diffraction pattern comprising the peak positions (degrees 2θ±0.2) when measured using Cu Kα radiation, of: 7.27, 8.98, 10.60, 15.60, and 23.93.

25. A solid form of (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl) cyclohexane-1-carboxylic acid, wherein the solid form is a hydrochloric acid addition salt, and wherein the hydrochloric acid addition salt is a hydrochloric acid addition salt characterized by an X-ray powder diffraction pattern comprising the peak positions (degrees 2θ±0.2) when measured using Cu Kα radiation, of: 7.27, 8.98, 10.60, 15.60, and 23.93.

26. A hydrochloric acid addition salt of (1R,3R)-3-((S)-2-((R)-(5-fluoro-2-methoxyphenyl)(hydroxy)methyl)-6-(methoxycarbonyl)-7-methyl-6,7,8,9-tetrahydro-3H-imidazo[4,5-f]quinolin-3-yl)cyclohexane-1-carboxylic acid.

27. The salt of embodiment 26, wherein the hydrochloric acid addition salt is Type A hydrochloric acid addition salt.

The invention claimed is:

1. A solid form of a hydrochloric acid addition salt of a compound of formula (II):

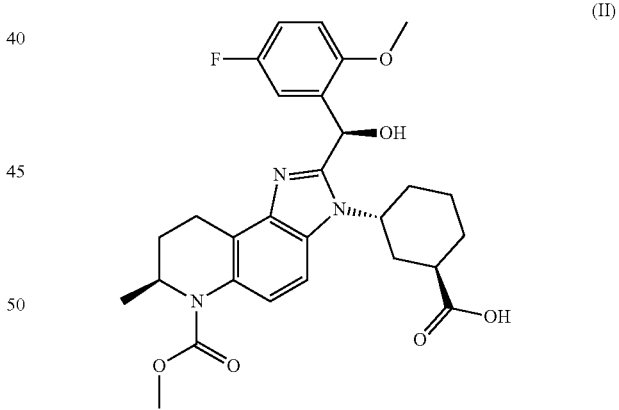

(II)

characterized by an X-ray powder diffraction pattern comprising at least three peak positions (degrees 2θ±0.2) when measured using Cu Kα radiation, selected from the group consisting of: 7.27, 8.98, 10.60, 15.60, and 23.93.

2. The solid form of claim 1, wherein the solid form is characterized by an endothermic peak having an onset temperature of about 230° C., as measured by differential scanning calorimetry.

3. The solid form of claim 1, wherein the solid form is characterized by a weight loss of about 1.1% at temperatures up to 170° C., as measured by thermogravimetric analysis.

4. The solid form of claim 1, wherein the solid form is an anhydrate.

5. The solid form of claim 1, wherein the solid form is hygroscopic.

6. The solid form of claim 1, wherein the solid form is stable for at least two weeks at temperatures up to 40° C. and relative humidity up to 75%.

7. A method for preparing a hydrochloric acid addition salt of a compound of formula (II):

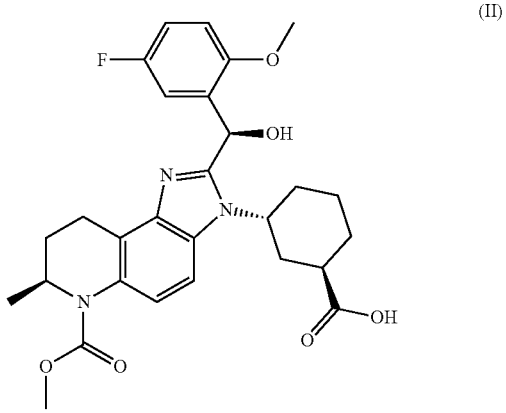 [SMILES: COC(=O)N1c2ccc3c(nc([C@H](O)c4cc(F)ccc4OC)n3[C@@H]3CCC[C@@H](C(=O)O)C3)c2CC[C@@H]1C]

comprising:
  dissolving the compound in an organic solvent, or a mixture of organic solvents to form a solution; and
  adding hydrochloric acid to the solution;
wherein the hydrochloric acid addition salt is characterized by an X-ray powder diffraction pattern comprising at least three peak positions (degrees 2θ±0.2) when measured using Cu Kα radiation, selected from the group consisting of: 7.27, 8.98, 10.60, 15.60, and 23.93.

8. The method of claim 7, wherein the organic solvent is ethyl acetate.

9. The method of claim 7, wherein the hydrochloric acid is at a concentration of about 37% w/v.

10. The method of claim 7, wherein the method further comprises heating the solution, optionally wherein heating the solution comprises heating the solution to a temperature of about 50° C.

11. The method of claim 10, wherein the method further comprises cooling the solution.

12. The method of claim 11, wherein cooling the solution comprises cooling the solution to a temperature of about 20° C. to about 25° C.

13. The method of claim 7, wherein the method further comprises filtering the solid form.

14. A pharmaceutical composition comprising the solid form of claim 1 and one or more of a pharmaceutically acceptable carrier, adjuvant, or vehicle.

15. A method of inhibiting one or more CBP/p300-family bromodomains in a patient comprising administering to the patient in need thereof a therapeutically effective amount of the solid form of claim 1.

16. A method of inhibiting one or more CBP/p300-family bromodomains in a patient comprising administering to the patient in need thereof a therapeutically effective amount of the pharmaceutical composition of claim 14.

17. A method of treating breast cancer in a patient comprising administering to the patient in need thereof a therapeutically effective amount of the solid form of claim 1.

18. A method of treating prostate cancer in a patient comprising administering to the patient in need thereof a therapeutically effective amount of the solid form of claim 1.

19. The hydrochloric acid addition salt of claim 1, wherein the hydrochloric acid addition salt is characterized by an X-ray powder diffraction pattern comprising the peak positions (degrees 2 θ±0.2), when measured using Cu Kα radiation, of: 7.27, 8.98, 10.60, 15.60, and 23.93.

* * * * *